United States Patent
Palacios et al.

(10) Patent No.: US 11,925,456 B2
(45) Date of Patent: Mar. 12, 2024

(54) SYSTEMS AND METHODS FOR SCREENING ASYMPTOMATIC VIRUS EMITTERS

(71) Applicant: HyperSpectral Corp., Alexandria, VA (US)

(72) Inventors: David M. Palacios, Pasadena, CA (US); Harry Hopper, Alexandria, VA (US)

(73) Assignee: Hyperspectral Corp., Alexandria, VA (US)

( * ) Notice: Subject to any disclaimer, the term of this patent is extended or adjusted under 35 U.S.C. 154(b) by 760 days.

(21) Appl. No.: 17/061,539

(22) Filed: Oct. 1, 2020

(65) Prior Publication Data
US 2021/0338100 A1 Nov. 4, 2021

Related U.S. Application Data

(60) Provisional application No. 63/080,653, filed on Sep. 18, 2020, provisional application No. 63/017,618, filed on Apr. 29, 2020.

(51) Int. Cl.
*A61B 5/08* (2006.01)
*A61B 5/00* (2006.01)
(Continued)

(52) U.S. Cl.
CPC ............ *A61B 5/082* (2013.01); *A61B 5/7282* (2013.01); *A61B 10/00* (2013.01); *G01J 3/18* (2013.01);
(Continued)

(58) Field of Classification Search
CPC ....... A61B 5/082; A61B 5/7282; A61B 10/00; A61B 5/097; A61B 2010/0087;
(Continued)

(56) References Cited

U.S. PATENT DOCUMENTS

2004/0239923 A1  12/2004  Adams et al.
2006/0281068 A1  12/2006  Maier et al.
(Continued)

FOREIGN PATENT DOCUMENTS

WO    2019089830 A1    5/2019

OTHER PUBLICATIONS

Giovannini et al. "Detecting COVID-19 from Breath: A game Changer for a Big Challenge." ACS sensors 6.4 (2021): 148-1417. Apr. 7, 2021 (Apr. 7, 2021), entire document [online].
(Continued)

*Primary Examiner* — Tarifur R Chowdhury
*Assistant Examiner* — Akbar H. Rizvi
(74) *Attorney, Agent, or Firm* — Ahmann Kloke LLP

(57) ABSTRACT

A method comprising at least one light source configured to generate a light of at least one wavelength and project the light over an optical path, a sample device, the device containing a sample obtained from exhalation of a person, a vortex mask configured to receive the light after the light passes through at least a portion of the sample device, the vortex mask including a series of concentric circles etched in a substrate, the vortex mask configured to provide destructive interference of coherent light received from the at least one light source, a detector configured to detect and measure wavelength intensities from the light in the optical path, the wavelength intensities being impacted by the light passing through the sample, the detector receiving the light that remained after passing through the vortex mask, and a processor configured to provide measurement results based on the wavelength intensities.

24 Claims, 31 Drawing Sheets

Screening allows only priority samples to be sent to labs to increase efficiency of the overall diagnostic lab testing system

(51) Int. Cl.
*A61B 5/097* (2006.01)
*A61B 10/00* (2006.01)
*G01J 3/18* (2006.01)
*G01J 3/45* (2006.01)
*G01N 1/42* (2006.01)
*G01N 21/25* (2006.01)
*G01N 21/3504* (2014.01)
*G01N 21/359* (2014.01)
*G01N 33/497* (2006.01)

(52) U.S. Cl.
CPC .................. *G01J 3/45* (2013.01); *G01N 1/42* (2013.01); *G01N 21/255* (2013.01); *G01N 21/3504* (2013.01); *G01N 21/359* (2013.01); *G01N 33/497* (2013.01); *A61B 5/097* (2013.01); *A61B 2010/0087* (2013.01); *G01N 2033/4975* (2013.01); *G01N 2201/063* (2013.01)

(58) Field of Classification Search
CPC ... A61B 5/7203; A61B 5/0075; A61B 5/0803; A61B 5/7246; G01J 3/18; G01J 3/45; G01N 1/42; G01N 21/255; G01N 21/3504; G01N 21/359; G01N 33/497; G01N 2033/4975; G01N 2201/063; G01N 21/31
See application file for complete search history.

(56) References Cited

U.S. PATENT DOCUMENTS

| | | |
|---|---|---|
| 2009/0103852 A1 | 4/2009 | Hamamoto |
| 2009/0148955 A1* | 6/2009 | Cunningham ....... G01N 21/253 |
| | | 436/164 |
| 2011/0028808 A1* | 2/2011 | Kuratsune ........... A61B 5/0059 |
| | | 600/322 |
| 2011/0270113 A1 | 11/2011 | Heyne et al. |
| 2016/0161404 A1 | 6/2016 | Marshall et al. |
| 2016/0377596 A1 | 12/2016 | Kusaba et al. |
| 2018/0067036 A1 | 3/2018 | Swartzlander, Jr. |
| 2018/0199137 A1 | 7/2018 | Mate et al. |
| 2018/0296123 A1 | 10/2018 | Karakaya et al. |
| 2020/0048721 A1 | 2/2020 | Jost et al. |
| 2020/0103406 A1 | 4/2020 | Holmes et al. |

OTHER PUBLICATIONS

International Search Report and Written Opinion for International Patent Application Serial No. PCT/US21/29441 dated Aug. 13, 2021.

* cited by examiner

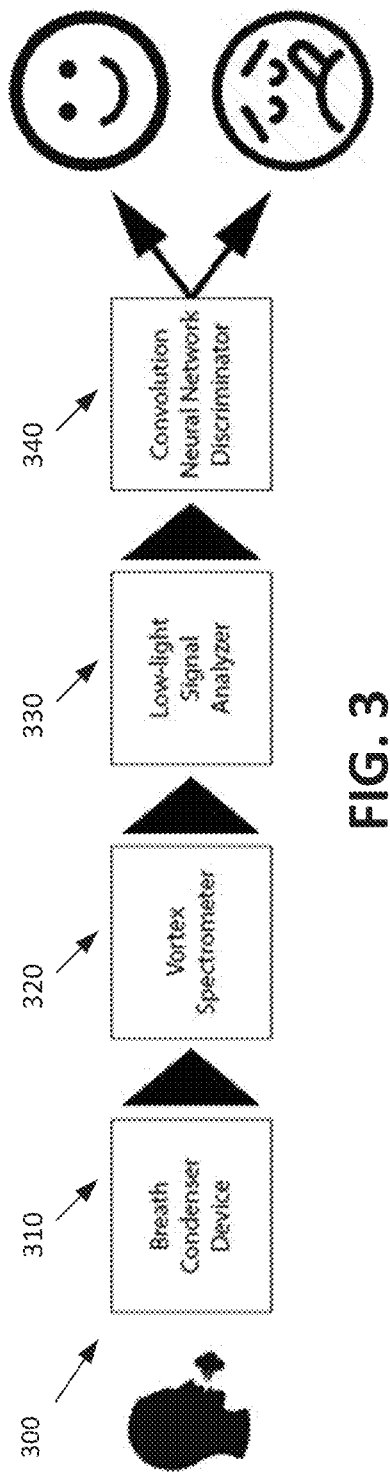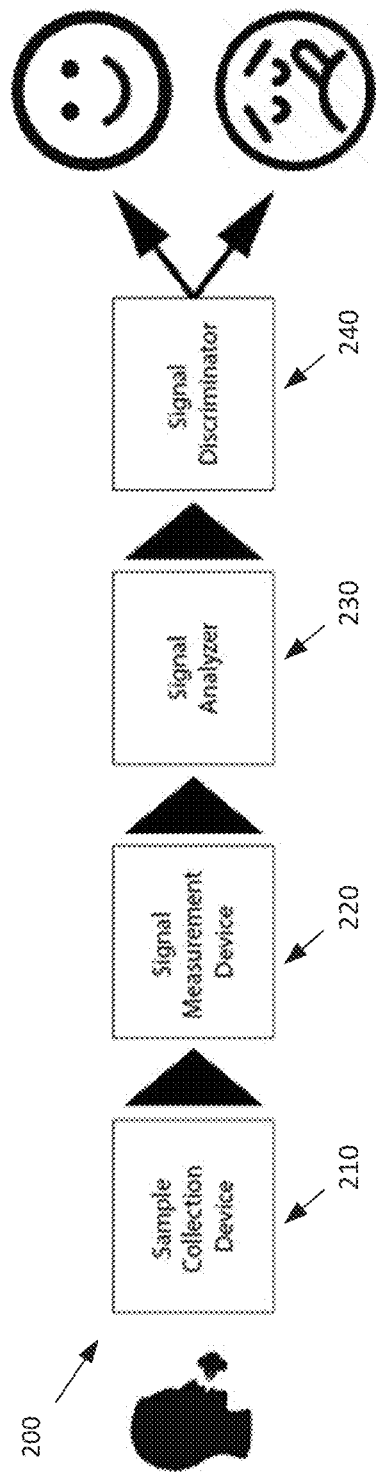

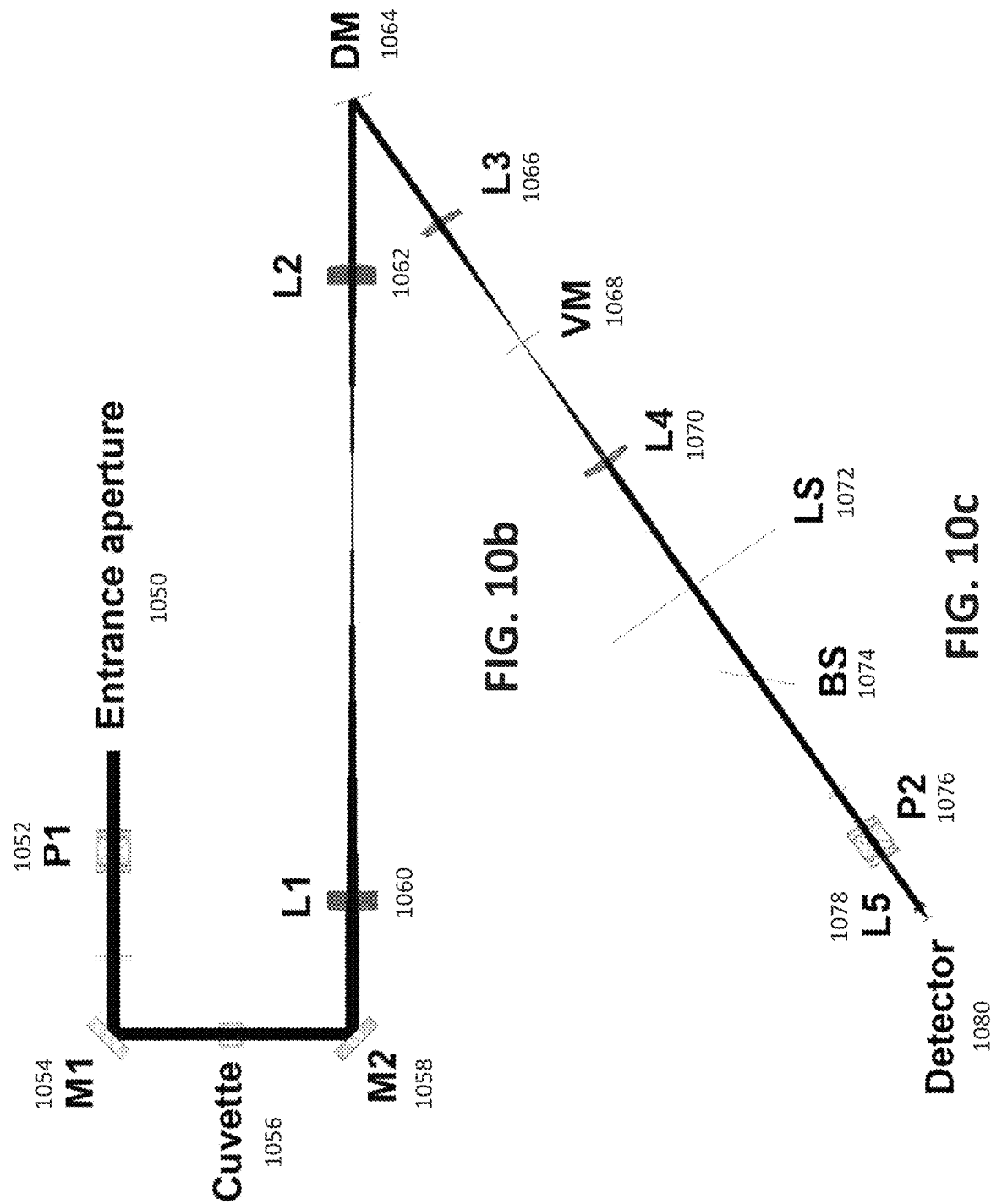

SYSTEMS AND METHODS FOR SCREENING ASYMPTOMATIC VIRUS EMITTERS

CROSS-REFERENCE FIELD

This application receives the benefit of U.S. Provisional Application No. 63/080,653, filed Sep. 18, 2020, entitled "SYSTEMS AND METHODS FOR SCREENING ASYMPTOMATIC VIRUS EMITTERS," and U.S. Provisional Application No. 63/017,618, filed Apr. 29, 2020, entitled "SYSTEMS AND METHODS FOR SCREENING ASYMPTOMATIC VIRUS EMITTERS" both of which are incorporated by reference herein.

TECHNICAL FIELD

This disclosure pertains to secure systems for noninvasive health screening and, more specifically, a spectrometer with a vortex mask to improve signal detection of infection of noninvasively acquired samples.

BACKGROUND

During a pandemic and the aftermath, it is vital to identify infected people so that they can be effectively quarantined to reduce the spread of the virus. Multiple testing methods have been developed to diagnose viral infections, including polymerase chain reaction (PCR), enzyme-linked immunosorbent assay, immunoflourescent assay, and others. However, these methods are impractical when it comes to wide-scale screening because of lack of speed, lack of accuracy, lack of resources, and cost. As seen with the COVID-19 pandemic, when attempting to screen large populations, reagent supplies become depleted, and current testing methodologies take days to return a result back to a patient. Due to the limited supply of test equipment, testing is performed on people who actively present symptoms and self-identify. The testing is primarily used to verify the diagnosis.

Relying on a person to present symptoms is a significant challenge for containment because of the reliance on a person's immune system's response to the virus (such as running a fever or developing a persistent dry cough). In the case of COVID-19, infected people may be contagious but asymptomatic during the virus' long incubation period (e.g., 2-14 days). The long incubation period has made the virus nearly impossible to contain and has required governments to take strong action to reduce the spread. These strong actions include orders for long-term shelter-in-place and social distancing until a vaccine can be developed and deployed globally (12-18 months).

SUMMARY

An example system comprising at least one light source configured to generate a light of at least one wavelength and project the light over an optical path, a sample device, the device containing a sample obtained from exhalation of a person, the sample device being transparent and being at least partially within the optical path, a vortex mask being within the optical path and configured to receive the light after the light passes through at least a portion of the sample device, the vortex mask including a series of concentric circles etched in a substrate, the vortex mask configured to provide destructive interference of coherent light received from the at least one light source, a detector configured to detect and measure wavelength intensities from the light in the optical path, the wavelength intensities being impacted by the light passing through the sample, the detector receiving the light that remained after passing through the vortex mask, and a processor configured to provide measurement results based on the wavelength intensities.

In some embodiments, the system further comprises a discriminator configured to analyze the measurement results and identify a category associated with the measurement results. The discriminator may utilize logistic regression to categorize the measurement results.

The sample may be obtained from a breathalyzer provided to a person. In one example, the breathalyzer cools a cuvette which condenses the sample of an exhalation of the user within the sample device, the sample device being removable from the breathalyzer.

The system may further comprise a Lyot mask (e.g., Lyot stop) positioned in the optical path and configured to receive light from the vortex mask and provide the light towards the detector, the Lyot mask configured to relocate residual light away from a region of the image plane, thereby reducing light noise from the at least one or more light sources and improving sensitivity to off-axis scattered light. The Lyot mask may be, for example, a Lyot-plane phase mask.

The vortex mask may be an optical vortex coronagraph that uses a phase-mask in which the phase-shift varies azimuthally around a center to mask out light along the center axis of the optical path of the spectrometer but allows light from off axis.

In various embodiments, the system comprises two light sources, each configured to provide a different wavelength. Alternately, the system may include a single light source that generates several wavelengths, the system further comprising a diffraction grating to separate out different wavelengths for propagating down the optical path.

In some embodiments, the at least one light source generates wavelengths at 735 nm, 780 nm, 810 nm, and 860 nm. The discriminator may assess features based on intensities of those wavelengths to make categories. In some embodiments, the sample may indicate infection by COVID-19.

An example method may comprise generating, by at least one light source, a light of at least one wavelength and project the light over an optical path, receiving, by a sample device, the light from the at least one optical source, the device containing a sample obtained from exhalation of a person, the sample device being transparent and being at least partially within the optical path, providing destructive interference of coherent light passed through the sample device using a vortex mask, the vortex mask including a series of concentric circles etched in a substrate, measuring, by a detector, wavelength intensities of the light after having passed through the vortex mask, and providing measurement results based on wavelength intensities.

BRIEF DESCRIPTION OF THE DRAWINGS

FIG. 2 is a generalized approach in some embodiments.

FIG. 3 is another example approach in some embodiments.

FIG. 10c is another example of an optical path of a spectrometer in some embodiments.

DETAILED DESCRIPTION

Figure 1:
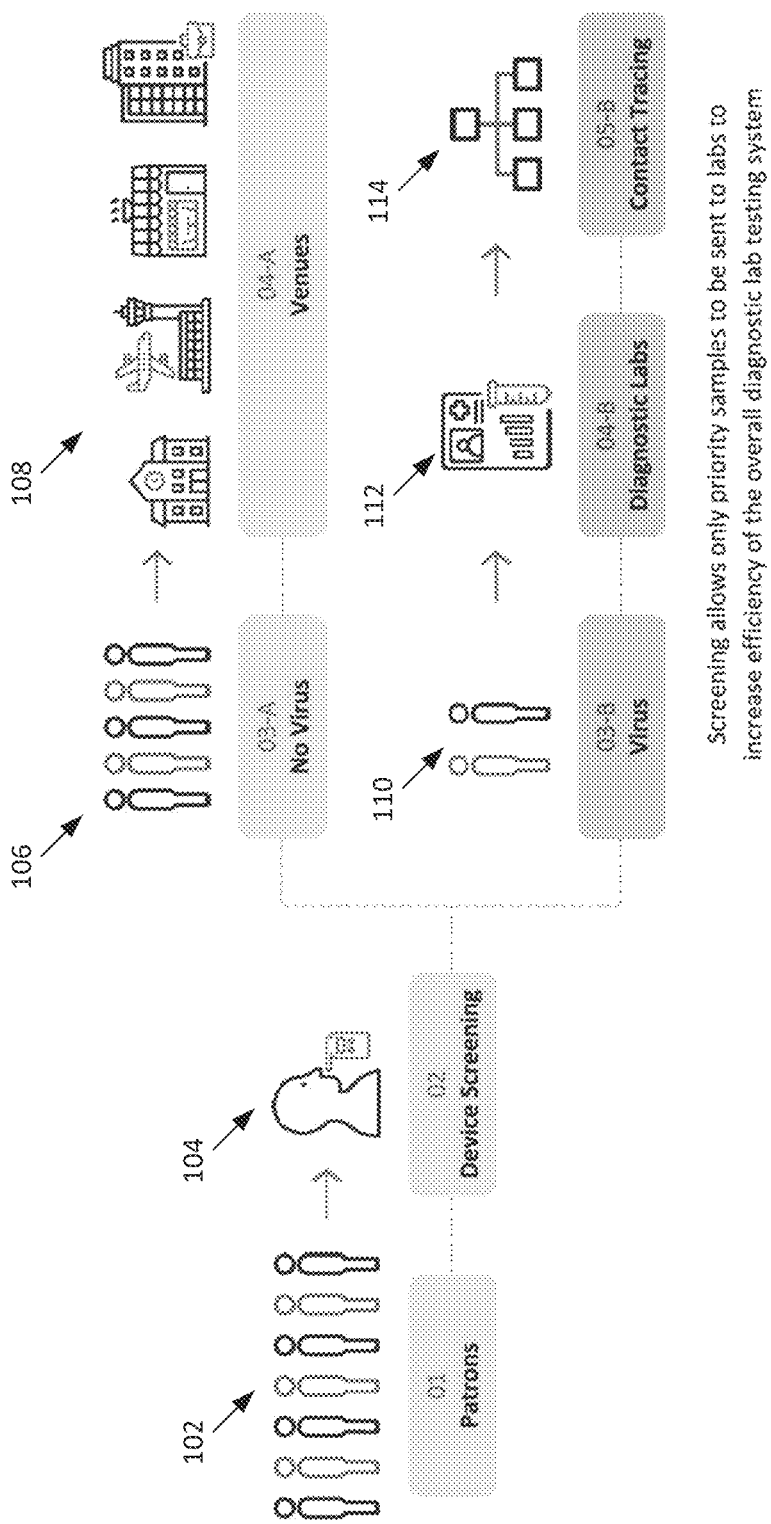
FIG. 1 depicts an environment for screening any number of patrons for infection in some embodiments.

Examples of health screening systems (HS systems) as discussed herein may enable early detection of infected people prior to those people presenting symptoms (i.e., prior to an immune system's reaction to the infection). The health screening system may be non-invasive, may require no reagents, and may return results quickly (e.g., within minutes or seconds). In different embodiments, the HS systems may test saliva, swabs, or a breath sample of a person.

In one example, the health screening system includes a spectrometer in communication with a data analysis discriminator (e.g., a statistical analytical discriminator and/or an artificial intelligence (AI) discriminator, which could be cloud-based and/or based on a smart device) that determines infection within minutes or less. In some implementations, the HS system described herein may allow for fast testing of large volumes of people with near real-time feedback on par with current airport security measures.

A noninvasive health screening device may include, for example, a breathalyzer or be coupled to a breathalyzer (e.g., a device that receives and collects the breath of a patron). Alternately, the health screening device may receive a saliva sample or a swab sample of a patron.

A spectrometer of the HS system may generate measurements based on absorption and/or transmittance of spectral components by particles of a sample provided by the patron. The measurements may subsequently be assessed in order to identify viruses, evidence of viruses (e.g., proteins), or other illnesses. Spectroscopy has not been applied to detect virus or other particles from the breath of a patron in the past because any information that may be gathered may be too faint (e.g., signals of interest based on the particles in breath are overwhelmed by the light of the spectroscopy as well as other aspects of the system).

In various embodiments, an example noninvasive health screening device may utilize a vortex filter (e.g., a vortex coronagraph) that may function to cause destructive interference of information in the spectrometer thereby amplifying an otherwise faded signal and enable assessments of the information provided by the spectrometer. Once the (otherwise previously faded) signal information is detected, information associated with viruses (e.g., based on spectral components associated with particles of interest in the patron's breath) may be assessed to determine if a patient is infected.

In some examples of COVID 19, a patron may provide a swab sample, a saliva sample, or exhale into a health screening device. Particles of the virus and/or proteins associated with the virus may be within the patron's sample. Proteins or other organic matter may be related to the virus directly or related to a body's respondence to infection or the physiological impact of infection. As discussed herein, prior to innovations described herein, spectral components of the particles of virus or proteins may not have been detectable due to their signals (e.g., based on light being shined through the breath sample) being too faint relative to other spectral components and/or light produced by the spectrometer.

FIG. 1 depicts an environment 100 for screening any number of patrons for infection in some embodiments. By utilizing a sample from the patron using systems and methods described herein, patrons may be screened for infection. Those without infection may, for example, be enabled to go to work, travel, engage in social functions, and/or attend events. Those with infections may be further assessed, treated, and/or place themselves in quarantine to prevent infection to others. Those with infection may also be provided with guidance to isolate themselves to the extent practical until the infection is overcome. It will be appreciated that utilizing the breathalyzer device as discussed herein in combination with the spectrometer with a vortex mask may enable detection of a virus and/or infection even if the patron is asymptomatic.

In the environment 100, there may be any number of patrons 102. A patron is any person of any age. Any group and/or any number of patrons may be tested for infection. Each patron may be tested with a health screening device 104.

The health screening device 104 may be non-invasive and requires no reagents. In various embodiments, the health screening device 104 or a system that assesses results from the health screening device 104, may return results within minutes or seconds. In one example, the health screening device 104 includes a deployable breathalyzer and spectrometer in communication with a discriminator (e.g., a cloud-based or local device) that determines the presence of infection. In other examples, the health screening device 104 includes a cuvette to collect a saliva sample or a device (e.g., fogging glass discussed herein) to receive a swab sample or saliva sample. The samples may be measured using a spectrometer as discussed herein and the results analyzed as also discussed herein. This system may allow for fast testing of large volumes of people with near real-time feedback on par with current airport security measures. The discriminator may be, or include, an artificial intelligence system (e.g., a convolutional neural network) or statistical classifier (e.g., a performing logistic regression).

In the example of environment 100, any number of patrons may be assessed at any number of locations. For example, patrons 102 may be screened prior to being allowed to enter to an office, place of employment, or venue 108. In another example, patrons 102 may be screened prior to being allowed to enter into any venue 108 such as an airport, plane, bus, bus terminal, train, train station, subway, subway station, retail store, restaurant, sports venue, concert venue, or the like. Because the health screening device 104 is noninvasive and may work quickly to detect infection, many geographically remote patrons may be effectively screened to enable them to engage in activities that may otherwise be unwise.

The results of the health screening device 104 may be assessed to determine if a patron is infected or not infected. Patrons that are determined not to be infected 106 may engage in activities that bring themselves into proximity with others (e.g., work, travel, entertainment, and the like). Patrons that are determined to be infected patrons 110, may be advised to maintain social distancing, receive treatment, and/or isolate themselves until they are no longer infected. Infected patrons 110 may be further tested by diagnostic labs 112 and/or be the subject of contact tracing 114 to identify other individuals that may be infected and may transmit the infection to others.

Due to the noninvasive nature and the speed of testing by the health screening device 104, infected patrons 110 may be repeatedly tested (e.g., every day), until it is determined that they have overcome the infection.

It will be appreciated with the increasing difficulty of obtaining traditional test kits (e.g., due to a limitation of the availability of certain reagents), health professionals may utilize the systems and methods described herein to determine infection and only use more traditional test kits on those with strong symptoms and/or those that are identified as being infected by the systems and methods described herein. Alternately, the systems and methods described herein may replace traditional testing.

FIG. 2 is a generalized approach 200 in some embodiments. Several examples includes receiving a breath sample using a breath condenser device. While these examples and some figures depict collecting a breath sample, it will be appreciated that a patron's saliva or swab sample may be collected instead of a breath sample. Samples (e.g., breath, saliva, or swab) may be utilized with one or more of the systems and methods described herein.

In step 210, a sample collection device (e.g., health screening device 104) receives breath (e.g., an exhalation) from a patron. As discussed herein, a patron is a person. The patron may or may not be sick with a viral infection. The patron may or may not show symptoms of infection. The sample collection device may be any collection device configured to receive an exhalation (e.g., breath) of a patron. The sample collection device may include or be coupled to a spectrometer. The spectrometer may be configured to project different wavelengths through particles of the breath of the patron in order to generate spectral components that may be measured.

In some examples, the sample collection device may include a breath collection chamber and/or a substrate. The breath collection chamber and/or substrate may be a transparent or semi-transparent member configured to collect particles from the breath of the patron. A spectrometer may project any number of wavelengths through the breath collection chamber and/or the substrate. The spectrometer may include or be coupled to a vortex mask in order to reduce or eliminate undesired wavelengths and/or wavelength intensities of the light that passed through the collection chamber and/or the substrate. The vortex mask may include or be an optical vortex coronagraph that uses a phase-mask in which the phase-shift varies azimuthally around the center. The vortex mask may use interference to mask out light along the center axis of the optical path of the spectrometer but allows light from off axis through. This enables scattered, incoherent light that interacted with components in the exhalation of the patron to pass through.

The signal measurement device 220 may be or include the spectrometer configured to receive and assess wavelength energy absorbed by and transmitted through the breath sample. In one example, a spectrometer may receive and project light into a chamber through an entrance aperture. The entrance aperture may be a lit which may vignette the light. In various embodiments, the spectrometer may include a filter to limit bandwidth of light entering the chamber. The light may reflect from a collimating mirror as a collimated beam towards a diffraction grating which may split photons by wavelength through an optical path. The diffraction grating may project the separated light through an exit slit or filter to control which wavelength is projected through the sample. In another example, the diffraction grating may spread the light across a focusing mirror which directs light at each wavelength through the breath collection chamber or the substrate to the detector. Light strikes the individual pixels of the detector. The detector may detect the transmittance and/or absorbance of the breath sample (i.e., the intensity of light along any number of wavelengths absorbed or transmitted).

The signal analyzer 230 may receive measurements from the detector of the signal measurement device 220 and provide an analysis of the measurements. The signal analyzer 230 may assess the measurements to identify information of interest (e.g., intensity of light absorbed and/or transmitted at specific wavelengths) while ignoring or assessing information from other wavelengths. The presence of certain wavelengths of a certain intensity in addition to or without other wavelengths may indicate the presence of proteins associated with one or more viruses.

The signal discriminator 240 may receive the analysis of the signal analyzer 230 to provide a category or indication of the presence of infection. In one example, the signal discriminator 240 may indicate whether a patron is infected or not infected. In another example, the signal discriminator 240 may indicate whether a patron is likely infected or not likely infected. In some embodiments, the signal discriminator 240 may indicate whether the infection status of the patron is unknown (e.g., if the analysis and/or discrimination is uncertain).

The signal discriminator 240 may be or utilize a logistic regression analysis model, model fitting, thresholding, an AI model (e.g., a neural network), and/or the like. In some embodiments, the signal discriminator maybe or utilize statistical and/or mathematical models to provide categories.

FIG. 3 is another example approach 300 in some embodiments. A breath condenser device 310 (e.g., breathalyzer 400 discussed herein) receives breath from a patron. A breath condenser device 310 may be configured to receive a person's breath from over a spigot, straw, or some other orifice. The breath from the patron may be collected on a transparent or semitransparent substrate (e.g., the breath may condense on the substrate). The breath condenser device 310 may have a heat sink, fan, coolant, and/or other elements to assist in the condensation of the user's breath.

The breath condenser device 310 may be any collection device configured to receive the breath of a patron and perform analysis on components and/or particles contained in the breath of the patron. The breath condenser device may include or be coupled to a spectrometer. The spectrometer may be configured to project different wavelengths through particles of the breath of the patron in order to generate spectral components that may be measured.

In various embodiments, the breath condenser device 310 is replaced with a fogging window for the patron to breath on (e.g., exhale), a cuvette to receive the patron's saliva, or the like.

Measurements on the condensed substrate may be taken using a vortex spectrometer 320. A vortex spectrometer 320 is a spectrometer with a vortex mask. The spectrometer 320 may be any spectrometer configured to project light at one or more wavelengths through the breath sample to a detector to make measurements based on absorption and/or transmittance.

The vortex mask, further discussed herein, may be a grating of concentric circles configured to create destructive interference and eliminate undesired light. This effect amplifies the desired signal from the proteins and/or viruses contained within the breath sample. As a result, a signal that is typically too faint to detect and is otherwise blocked out by other signals (i.e., noise) becomes detectable.

The low-light signal analyzer 330 may be a signal measurement device and/or a signal analyzer configured to work in conjunction with the vortex mask to identify faint signals that are created or influenced by the presence of proteins and/or viruses in the breath samples. The low-light signal analyzer 330 may be or include the spectrometer configured to receive the assess wavelength energy absorbed and transmitted through the breath sample.

The low-light signal analyzer 330 assesses the measurements to identify information of interest (e.g., intensity of light absorbed and/or transmitted at specific wavelengths) while ignoring or assessing information from other wavelengths. The presence of certain wavelengths of a certain intensity in addition to or without other wavelengths may indicate the presence of proteins associated with one or more viruses.

The convolutional neural network discriminator 340 may receive the analysis from the low-light signal analyzer 330 to provide a category or indication of the presence of infection. As discussed regarding FIG. 2, a signal discriminator may be any device or include any approach for assisting in categorizing infection. In this example, the signal discriminator is a convolutional neural network discriminator 340.

The convolutional neural network discriminator 340 may be trained based on at least a subset of measurements and analysis generated from any number of peoples' condensed breath and the known results (e.g., infection confirmed and/or lack of infection confirmed through lab testing or other means). Once trained, the convolutional neural network discriminator 340 may be tested against a subset of analysis and measurements of people to compare the prediction to known truth. The convolutional neural network discriminator 340 is further described herein.

In one example, the signal discriminator 240 may indicate whether a patron is infected or not infected. In another example, the signal discriminator 240 may indicate whether a patron is likely infected or not likely infected. In some embodiments, the signal discriminator 240 may indicate whether the infection status of the patron is unknown (e.g., if the analysis and/or discrimination is uncertain).

The signal discriminator 240 may be or utilize an AI model (e.g., a neural network) that is trained and curated. In some embodiments, the signal discriminator maybe or utilize statistical and/or mathematical models to provide categories.

Figure 4A:
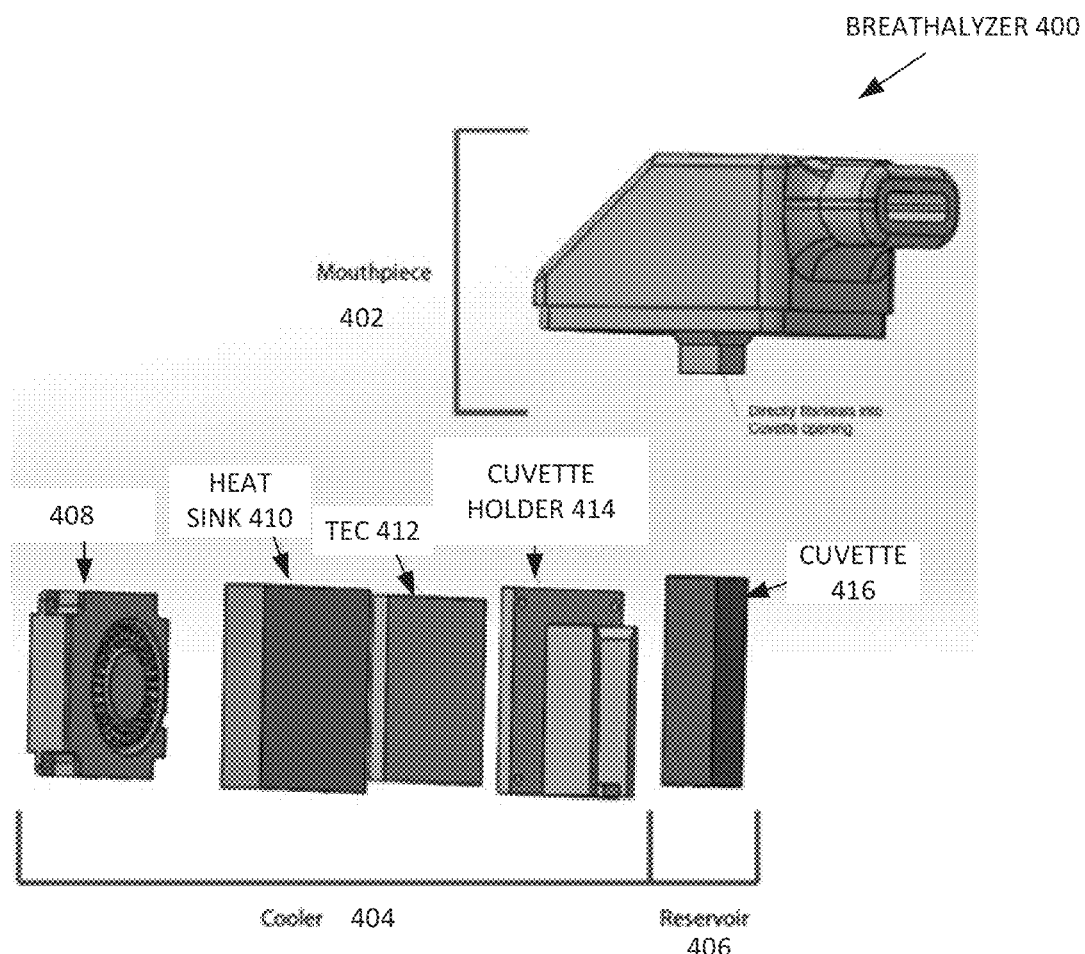
FIG. 4*a* depicts an example breathalyzer in some embodiments.

FIG. 4a depicts an example breathalyzer 400 in some embodiments. The breathalyzer 400 may enable a patron to breath through a mouthpiece 402. The breathalyzer 400 may receive a sample of the patron's breath. A spectrometer may receive the sample for analysis. The sample may be rejected from the breathalyzer 400 or the breathalyzer 400 may be coupled to or within the spectrometer.

In the example breathalyzer 400 of FIG. 4a, the breathalyzer 400 is hand-sized. The breathalyzer 400 may include a mouthpiece 402, a cooler 404, and a reservoir 406. The example breathalyzer 400 is configured to receive the breath of the patron through the mouthpiece 402 and preserve samples from the breath of the patron in the reservoir 406. It will be appreciated that there may be many ways in which to collect and hold the breath sample. In this example, the cooler 404 assists to collect particles of interest of the breath of the patron by cooling the cuvette and allowing the particles (e.g., within or bound to moisture in the breath sample) to collect on a surface inside the cuvette.

In the example of the breathalyzer 400, the cooler 404 includes a fan 408, a heat sink 410, a thermoelectric cooler (TEC) 412, and a cuvette holder 414. The reservoir 406 includes the cuvette 416. The breathalyzer 400 may be hand-sized or be able to be manipulated and/or controlled with one or two hands. The breathalyzer 400 may include an outer housing that houses the cooler 404 and/or the reservoir 406. The mouthpiece 402 may be coupled to the housing. The housing may be made of plastic or other material. The outer housing may hold the components of the cooler 404 and the reservoir 406. The outer housing may also include a portal or lid which can be opened and the cuvette 416 removed from the breathalyzer 400. A new cuvette 416 may also be inserted into the breathalyzer 400 through the portal or lid.

In various embodiments, the mouthpiece 402 may include a conduit that is sealed directly to the cuvette 416 opening or through a conduit or other component that allows for a direct air path from the mouthpiece 402 to the cuvette 416. In various embodiments, the mouthpiece 402 is removable from the housing of the breathalyzer 400 and may be replaced or cleaned after being used by one or more patrons. In one example, a patron may blow through a hole in the mouthpiece to direct air into the cuvette 416. A sample of the patron's breath may be held in the cuvette 416. The cuvette 416 may be ejected and/or the mouthpiece replaced with a new mouthpiece prior to the next patron breathing into the breathalyzer 400.

In various embodiments, the conduit and/or the mouthpiece 402 may include pressure release air passages to allow air to escape as the patron blows through the mouthpiece 402. In various embodiments, the cuvette 416 may include an air escape conduit to allow air to pass through the cuvette 416 and collect the sample. The air escape conduit may include a filter to prevent virus particles or the like from escaping the breathalyzer 400. In some embodiments, the air escape conduit may include a flap or other technique to prevent air from flowing from the outside the breathalyzer 400 back into the cuvette 416.

The cuvette 416 may be an optically clear container for holding samples (e.g., samples of the patron's breath). The cuvette 416 may be transparent or hold a removable sample substrate that is transparent. In various embodiments, the cuvette 416 is removable from the breathalyzer 400. In various embodiments, the cuvette 416 may be placed within a spectrometer or within the light beams of a spectrometer in order for a detector and analyzer to analyze absorption and/or transmittance.

In various embodiments, a spectrometer (e.g., a vortex spectrometer) may include a lid or portal to allow the cuvette 416 to be inserted into and/or removed from the optical path of the spectrometer. The cuvette may be replaced with another cuvette containing a different breath sample from a different patron after each analysis. In some embodiments, multiple tests are run on the same cuvette to enable multiple measurements (e.g., "data snapshots"). This process may be used in conjunction with "lucky imaging" discussed herein to improve accuracy.

The cooler 404 may contain a fan 408 that directs air into or air out of the breathalyzer 400. The fan may be powered by a battery that is now shown in FIG. 4A or 4B. The battery may also power the TEC 412. The battery may run on any batteries such as commercial batteries, retail batteries, lithium ion, polymer, and/or the like.

A heat sink 410 may include a block of 17hermos-conductive material with or without fins to pull heat from the TEC 412. The fan 408 may remove heat form the heat sink 410 to assist in cooling. In various embodiments, the outer housing of the breathalyzer 400 may include slits or other air passages to allow hot air to pass out of the breathalyzer 400.

The TEC 412 may be any thermoelectric cooler that operates by the Peltier effect by creating a temperature difference between two electrical junctions. As voltage is applied across joined conductors, a current is induced that flows through the junctions of two conductors. Heat is removed at one junction (thereby creating cooling in that junction) and collects in the other. Heat is then transferred from the heated junction to the heat sink 410 which is subsequently cooled by the fan 408. It will be appreciated that the TEC 412 is optional (e.g., the cuvette 416 and/or the cuvette holder 414 may be in contact with the heat sink 410).

The cuvette holder 414 may be coupled between the cuvette 416 and the TEC 412. The cuvette holder 414 may be in contact with the TEC 412 to pull heat away from the cuvette 416. The TEC 412 may removably hold the cuvette 416 into position and enable the cuvette 416 to be removed and replaced (e.g., through the outer housing). The cuvette holder 414 may include a conductive surface to pull heat away from the cuvette 416.

In various embodiments, the cuvette 416 is cooled which will cause the breath sample of the patron to condense along the inside walls or substrate of the cuvette 416.

While the breathalyzer 400 is depicted as hand-sized, it will be appreciated that samples of the breath of a patron may be taken in any number of ways. For example, the patron may breathe into a mouthpiece which directs the patron's breath to pane of transparent plastic (e.g., within or outside of a cuvee). The pane of transparent plastic may subsequently be used within a spectrometer (e.g., the mouthpiece may be coupled by a conduit to the pane of transparent plastic which may be within or coupled to a spectrometer). After the sample is analyzed by the spectrometer or digital device in communication with the spectrometer, then the pane of transparent plastic may be replaced or washed (e.g., with an alcohol solution or the like) to prepare for the next patron.

As discussed herein, the systems and methods described herein are not limited to utilizing breath samples of a breathalyzer.

Figure 4B:
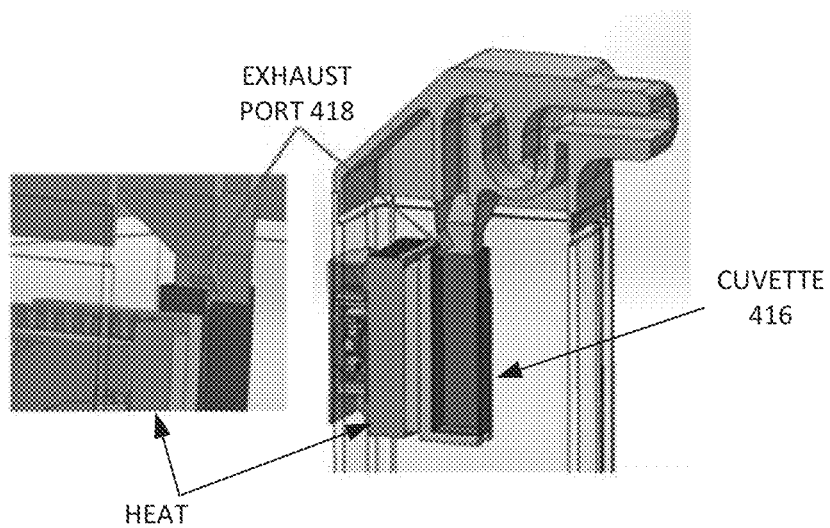
FIG. 4*b* is another view of the breathalyzer in some embodiments.

FIG. 4b is another view of the breathalyzer 400 in some embodiments. FIG. 4b depicts the breathalyzer 400 coupled. The cuvette 416 and/or the mouthpiece 402 may include an exhaust port 418 to assist with air escape and allow the sample to be collected. The exhaust port 418 may include a filter to prevent virus particles or the like from escaping the breathalyzer 400. In some embodiments, the exhaust port 418 may include a flap or other technique to prevent air from flowing from the outside the breathalyzer 400 back into the cuvette 416. The exhaust port 418 may allow for air from the breath of the patron to escape and be pushed out of the breathalyzer 400 by the fan 408 (e.g., through slits or openings of the outer housing which may or may not be filtered).

While a breathalyzer 400 is depicted in FIG. 4, it will be appreciated that a sample of a patron may be taken in many different ways and used with systems described herein. For example, a patron may breath into the breathalyzer 400, provide a swab and the swab used to apply the patient's fluids to a transparent substrate, or provide saliva which is applied to the transparent substrate. Any or all of these approaches may be used with the spectrometer with a vortex mask as described herein.

Figure 5:
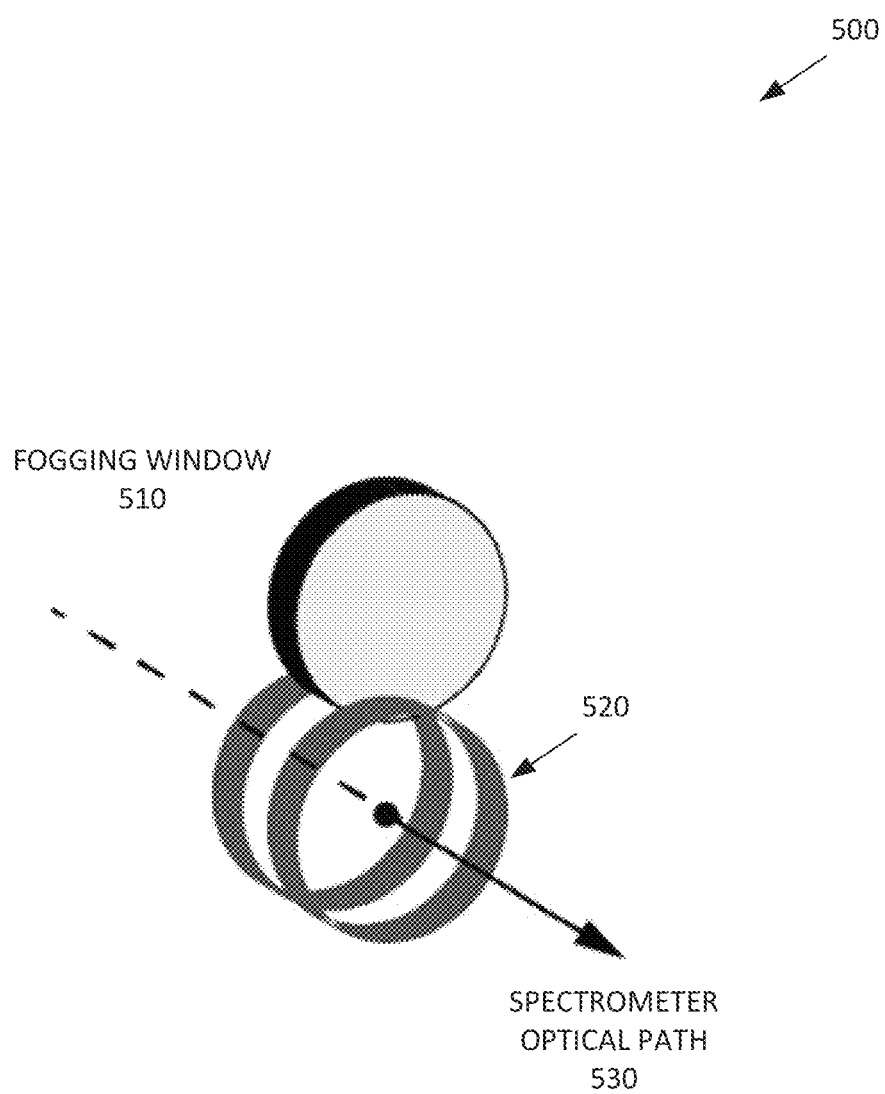
FIG. 5 depicts transparent substrates for collecting a sample a patron.

FIG. 5 depicts transparent substrates 500 for collecting a sample from a patron. The transparent substrates 500 may be utilized to collect a breath sample (e.g., the patron exhaling on at least one of the transparent substrates 500), a saliva sample (e.g., applying the patron's saliva to at least one of the transparent substrates 500), or a swab sample (e.g., applying the residue from a swab sample on at least one of the transparent substrates 500).

The transparent substrates 500 may include a fogging window 510 and transparent members 520. In one example, the patron may breath or exhale on the fogging window 510. The transparent members 520 and/or the fogging window 510 may be cooled to collect moisture and particles from the user's sample.

The fogging window 510 may be coupled (e.g., rotationally coupled to a pin at or near a common edge) to the transparent members 520. In some embodiments, the fogging window 510 may be rotationally coupled to the transparent members 520. In one example, the fogging window 510 may be rotationally coupled by a peg or a point connected to both the transparent members 520 (e.g., along an edge) to allow the fogging window 510 to rotate out of being between the transparent members 520. In one example, the fogging window 510 may be rotated away from the transparent members 520 to allow a patron to exhale on the fogging window 510 without exhaling on the transparent members 520. After the fogging window 510 has collected a sample of the patron's breath, the fogging window 510 may rotate along the coupling point between the transparent members 520.

The transparent substrates 500 may then be inserted or coupled to a spectrometer. The spectrometer optical path 530 is a path for light projected by the spectrometer to a detector. In some embodiments, the spectrometer may have a portal or lid that allows the transparent substrates 500 to be inserted for analysis (e.g., as the sample cell) and then removed to make room for another set of transparent substrates 500 containing another breath sample from another patron.

The transparent members 520 may be made of any transparent material including, for example, glass or plastic. There may be any number of transparent members 520 (e.g., one or more)

In some embodiments, the transparent substrates 500 and/or the fogging window 510 may be contained in the breathalyzer 400 and/or the cuvette 416. In other embodiments, the transparent substrates 500 may be unrelated to the breathalyzer 400. In this example, the transparent substrates 500 may be handled by a health professional wearing gloves and allow the patron to exhale on the fogging window 510.

There may be any number of fogging windows 510. For example, the transparent substrates 500 may include pairs of transparent members 520 with a fogging window 510 between each pair (e.g., fogging windows 510 between a pair of transparent members 520). Each fogging window 510 may be rotationally coupled to the transparent members 520 to enable each fogging window 510 to rotate out from between the transparent members 520 independent of other plane windows 510.

In another example, there may be any number of fogging windows connected by the common pin. While one of the fogging windows 510 may be between the two transparent members 520, the other two fogging windows 510 may be outside the two transparent members 520. A first fogging window 510 between the two transparent members 520 may be placed within an optical path of a spectrometer. After measurements are taken, the transparent substrates 500 may be removed and the fogging window 510 rotated such that a second fogging window 510 may be placed between the two transparent members 520 and placed within the spectrometer. After measurements of the second sample of the second fogging window 510 is taken, the transparent substrates 500 may be removed and the second fogging window 510 rotated such that a third fogging window 510 may be placed between the two transparent members 520 and placed within the spectrometer for additional measurements. Each fogging window 510 may contain a sample from a different patron or, in some embodiments, each fogging window 510 may contain a different breath sample from a different patron.

After analysis, the fogging window 510 and/or the transparent members 520 may be cleaned or washed (e.g., using an alcohol-based solution, soap, and/or the like).

Figure 6:
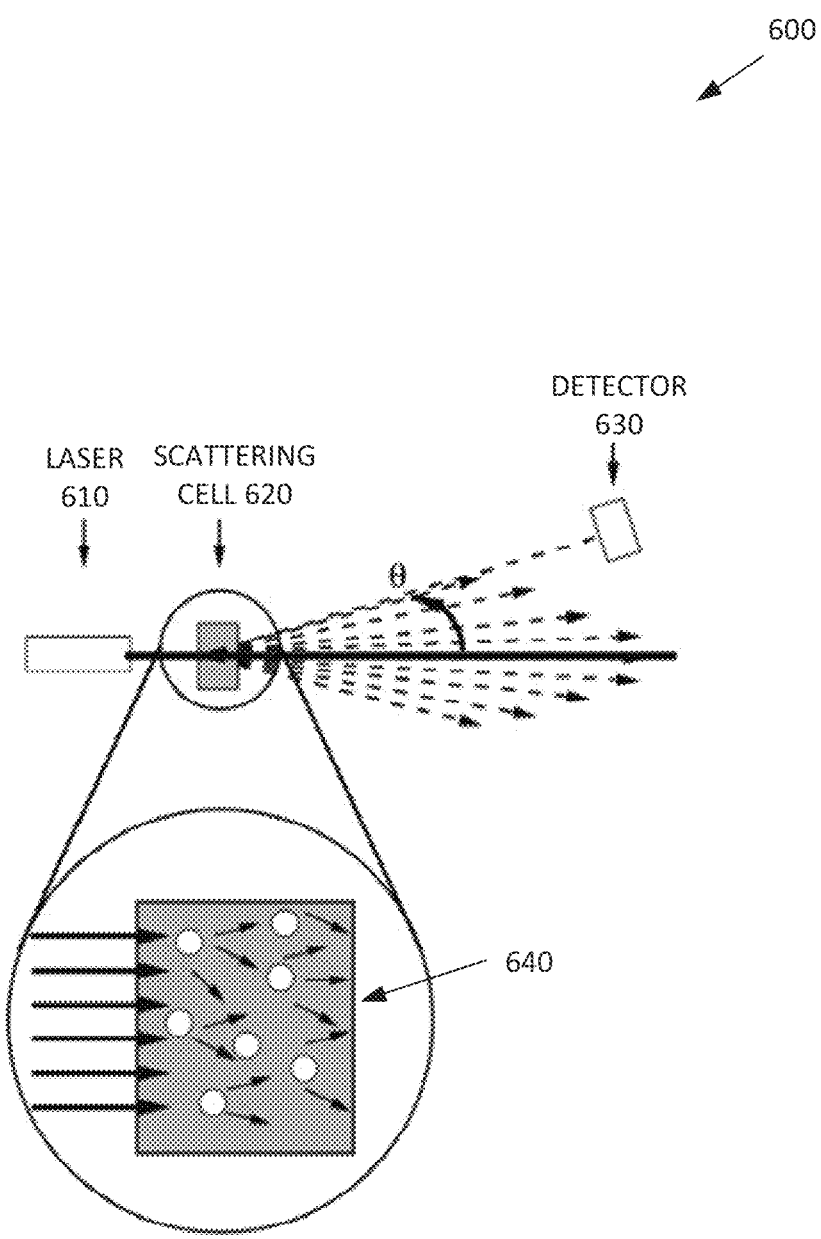
FIG. 6 depicts an absorption and scattering diagram in some embodiments.

FIG. 6 depicts an absorption and scattering diagram 600 in some embodiments. The absorption & scattering diagram 600 may depict a process that occurs within the spectrometer. In this example, a laser 610 may project light along an optical path through the scattering cell 620. Scattering cell 620 may contain, for example, the cuvette 416, the transparent substrates 500, or the like. Light from the laser 610 may be absorbed and scattered as depicted in view 640. A detector 630 may be positioned such that the detector receives scattering of light at the desired wavelength.

Figure 7:
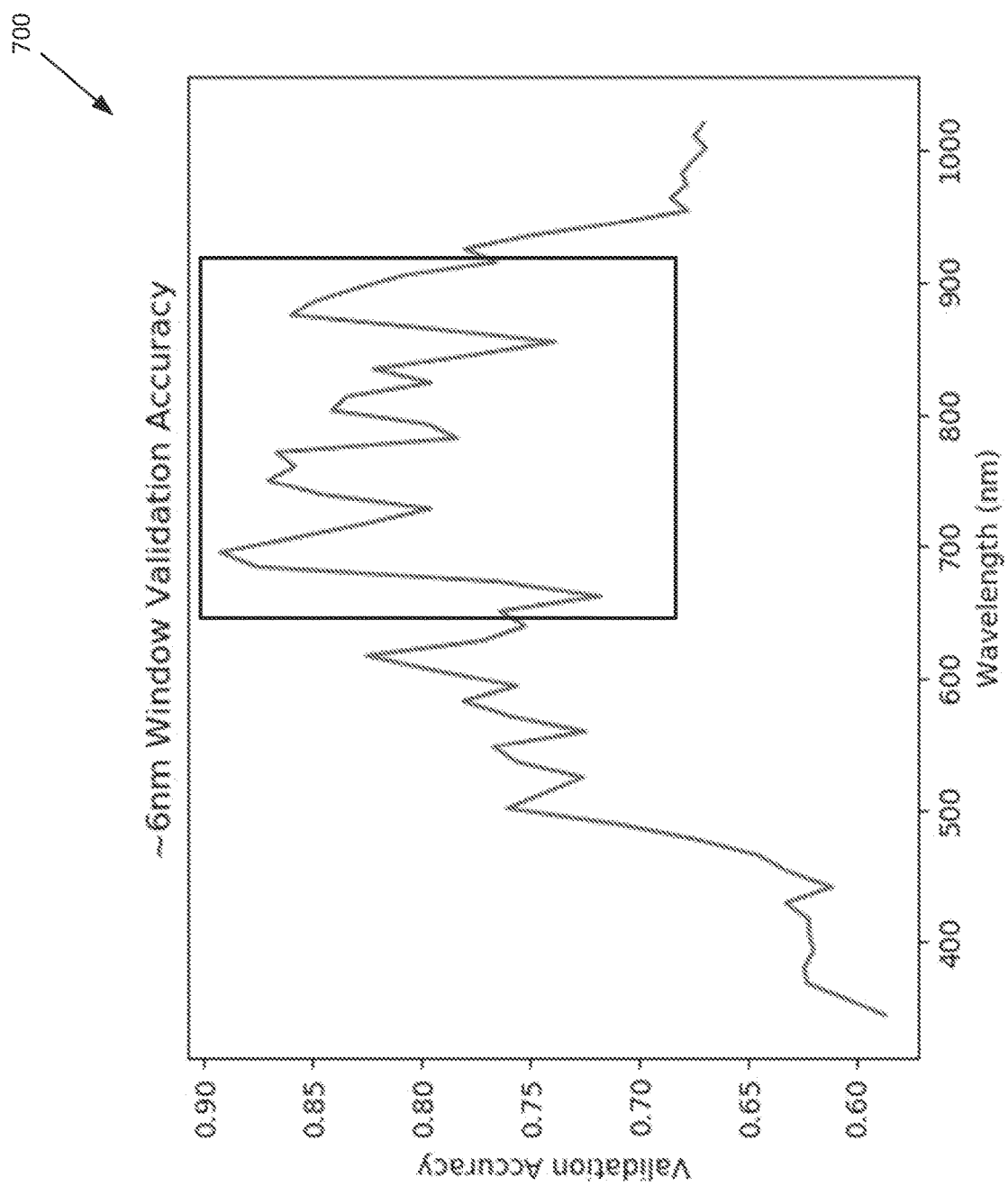
FIG. 7 depicts a window validation accuracy graph in some embodiments.

FIG. 7 depicts a window validation accuracy graph in some embodiments. In some embodiments, the output of the spectrometer may be or appear similar to the graph 700. In some embodiments, peaks of wavelength intensities at 735 nm, 780 nm, 810 nm, and 860 nm may suggest or indicate infection.

Figure 8:
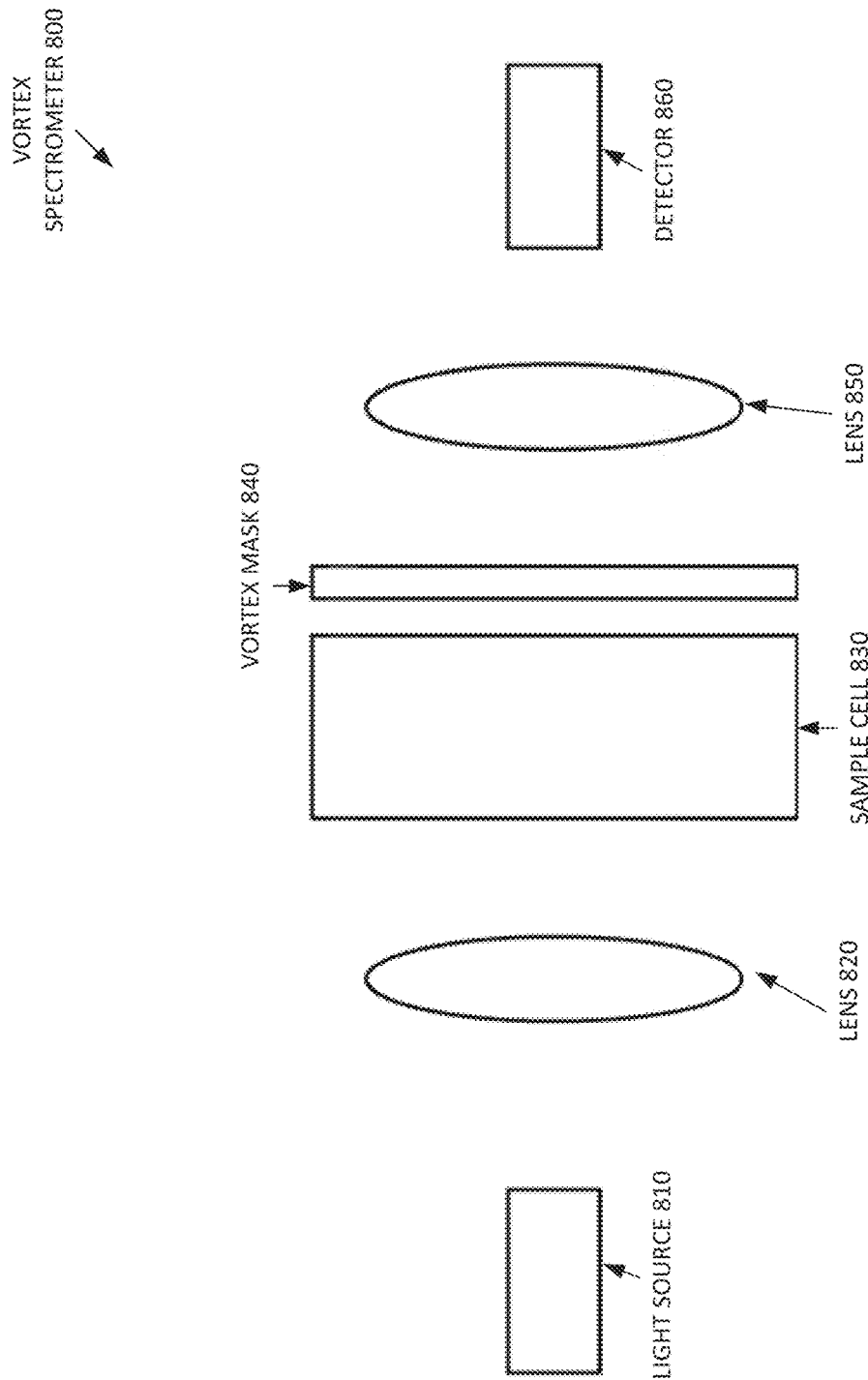
FIG. 8 depicts an example vortex spectrometer in some embodiments.

FIG. 8 depicts an example vortex spectrometer 800 in some embodiments. The spectrometer depicted in FIG. 8 is simplified. It may be appreciated that the spectrometer may include an aperture for controlling wavelengths, filters, beam splitters, diffraction grating, and the like as discussed herein.

The vortex spectrometer 800 of FIG. 8 includes a light source 810 (e.g., laser), first lens 820, sample cell 830, vortex mask 840, a second lens 850, and a detector 860. Light from a broadband light source 810 may be collimated by lens 820. The collimated light passes through a sample cell (e.g., containing the condensed breath of a patron), a vortex mask 840, and the second lens 850 before passing to the detector 860.

When the light passes through a scattering medium containing particles larger than the wavelength, light is scattered. The most intense scattering usually occurs in the forward direction. Light scattered along the optical axis is often difficult to distinguish from the superimposed unscattered laser beam, especially when there is a dilute concentration of weak scatterers. This scattered light may interfere with the light of the principle beam and, as a result, speckle (i.e., noise) may be formed.

In some cases, particular wavelengths may be absorbed by the scattering media. This occurs because the light at those particular wavelengths excite the rotational or vibrational state of the molecules in the media. Therefore, the chemical makeup of an absorbing media may be determined from the spectral absorption signature that is present. If the medium is weakly scattering (i.e., there are few scatterers), the absorption signature may be overwhelmed by the strong on-axis unscattered light source. Therefore, in order to optimize the characterization of the scattering molecules, a light suppression technique may be utilized to attenuate the strong on-axis source while leaving the weaker scattered signal intact.

An optical vortex 840 is a dark null of destructive interference that occurs at a spiral phase dislocation in a beam of spatially coherent light. The phase of a transmitted light beam may be twisted and light from opposite sides of the mask may coherently destructively interfere to form a dark null in the transmitted intensity pattern, much like the eye of a hurricane.

The vortex mask 840 may assist to create destructive interference of the light source, thereby enabling improved sensitivity of fainter signals. In one example of the optical path shown in FIG. 8, light is projected from the light source 810 through the breath collection chamber and/or transparent member. The light then passes through the vortex mask 840 to be detected by the detector 860 which digitizes the signal as a function of wavelength and provides the signal for further analysis and/or display.

In some embodiments, divergent light may be collimated by a concave mirror and directed into a grating to disperse the spectral components of the light at slightly varying angles which may be focused by a second concave mirror and imaged onto a detector.

The vortex mask 840 may be a vortex coronagraph configured to reduce unwanted glare from a spectrometer light source. As discussed herein, the spectrometer may include or be coupled to a vortex mask in order to reduce or eliminate undesired wavelengths and/or light intensities of the light that passed through the sample cell 830. The vortex mask 840 may include or be an optical vortex coronagraph that uses a phase-mask in which the phase-shift varies azimuthally around the center. The vortex mask 840 may use interference to mask out light along the center axis of the optical path of the spectrometer but allows light from off axis.

A vortex mask 840 may be used to create an optical vortex to reduce or eliminate unwanted light from the spectrometer light sources. Without reducing undesirable light from the spectrometer light sources, many signals may otherwise be too faint to be detected (e.g., faint signals from desired absorption or transmittance is overwhelmed by the other signals caused by the light sources).

In some embodiments, the vortex mask 840 may be or utilize an optical vortex coronagraph. An example optical vortex coronagraph uses a helical phase of the form $e_{i\phi}$, with $\phi=l\theta$, where l is the topological charge and $\theta$ is the focal plane azimuthal coordinate. In optical systems, vortices manifest themselves as dark donut of destructive interference that occur at phase singularities. For example, $E(\rho, \phi, z, t)=A(\rho, z) \exp(il\theta) \exp(i\omega t-ikz)$ where $(\rho, \phi, z)$ are cylindrical coordinates, $A(\rho, z)$ is a circularly symmetric amplitude function and $k=2\pi/\lambda$ is the wavenumber of a monochromatic field of wavelength $\lambda$.

In some embodiments, the optical vortex coronagraph may utilize a rotationally symmetric half wave plate which can generate an azimuthal phase spiral reaching an even multiple of 2pi radian.

The vortex mask 840 may include an optical vortex induced by an achromatic subwavelength grating. In some embodiments, the vortex mask 840 maybe an annular groove phase mask coronagraph. As discussed herein, without the vortex mask 840, detection of faint sources around significant noise may be difficult due to the large ratio between them.

In various embodiments, the vortex mask 840 is not a pure amplitude mask, a pure phase mask, a single pupil achromatic nulling interferometer, or a monochromatic pupil plane mask. In one example, the vortex mask 840 may be an annular groove phase mask coronagraph. The vortex mask 840 may include a focal plane that is divided into four equal areas centered on an optical axis. Unlike a mask where two of the focal planes are on a diagonal providing a $\pi$ phase shift to cause destructive interference inside a geometric pupil area, the vortex mask 840 utilizes subwavelength gratings while suppressing "dead zones" (e.g., where potential circumstellar signal or companion is attenuated by up to 4 magnitudes). The vortex mask 840 may include concentric circular subwavelength gratings.

Figure 9A:
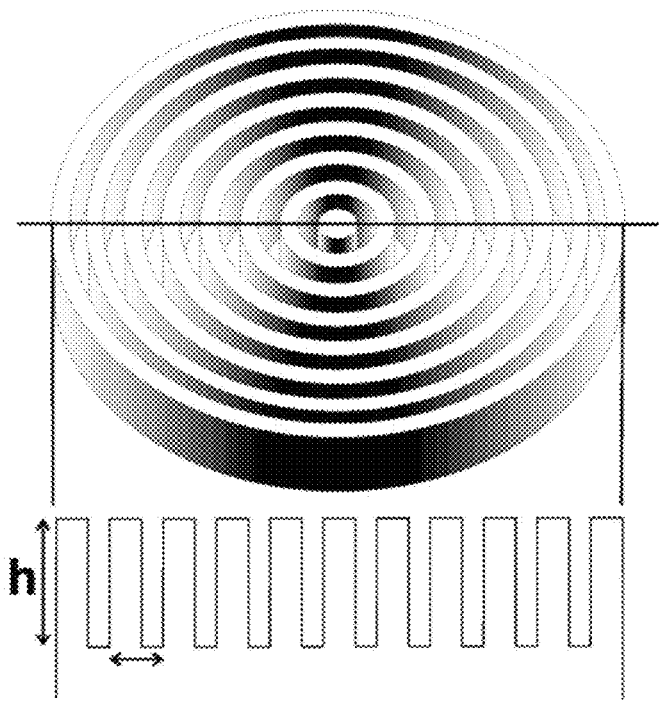
FIG. 9a depicts an example coronagraph scheme including a concentric circular surface relief grating with rectangular grooves with depth h and a periodicity of A.

The vortex mask 840 may include a focal plane microcomponent including a concentric circular surface-relief grating with rectangular grooves of depth h and equally separated by a period A. FIG. 9a depicts an example coronagraph scheme including a concentric circular surface relief grating with rectangular grooves with depth h and a periodicity of A. In some embodiments, the vortex mask 840 may be a vectorial phase mask (i.e., the vortex mask 840 induces a differential phase shift between the local polarization states of the incident natural (or polarized) light).

When the period A of the grating is smaller than the wavelength of the incident light, the vortex mask 840 does not diffract as a classical spectroscopic grating. Incident energy is enforced to propagate only in the zeroth order, leaving incident wavefronts free from any further aberrations. In various embodiments, the subwavelength gratings of the vortex mask 840 may be Zeroth Order Gratings.

Figure 9B:
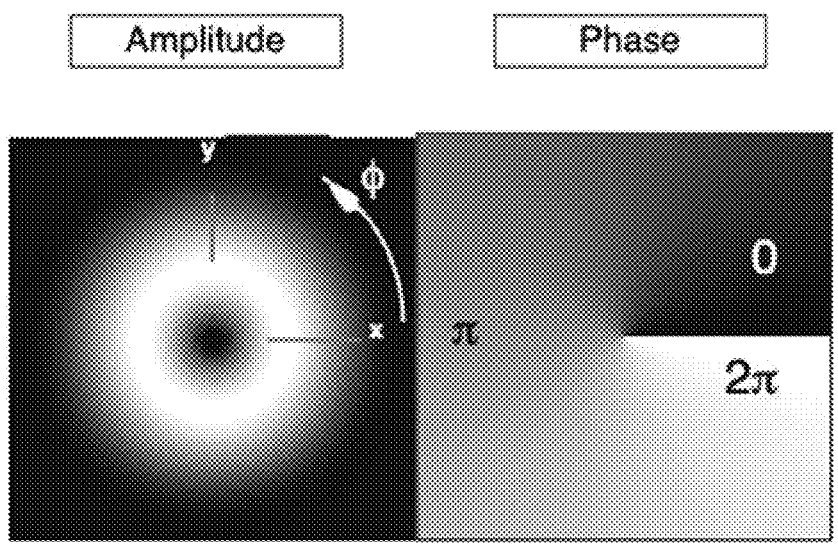
FIG. 9b includes images of amplitude and phase caused by the vortex mask in some embodiments.

By controlling the geometry of the grating structure, the vortex mask 840 may be tuned (e.g., to make the form birefringence proportional to the wavelength in order to achromatize the subsequent differential 7L phase shift between two polarization states). This may create an optical vortex where phases possess a screw dislocation inducing a phase singularity. The central singularity forces the intensity to vanish by a total destructive interference, creating a dark core. This dark core propagates and is conserved along the optical axis. In various embodiments, the vortex mask 840 creates an optical vortex in the focal plane, filtering in the relayed pupil plane and making the detection in a final image plane. FIG. 9b includes images of amplitude and phase caused by the vortex mask 840 in some embodiments.

In various embodiments, the vortex mask 840 may be fabricated by imprinting the concentric annular mask in a resin coated on a chosen substrate material. For example, fabrication may be performed, in party, by laser direct writing or e-beam lithography. This process may define the lateral dimensions of the Zeroth Order Gratings (ZOG). This pattern may then be uniformly transferred in the substrate by an appropriate reactive plasma ion beam etching down to the desired depth.

In some embodiments, a space-variant half-wave plate may be used to generate the optical vortex. In one example, A beam of light containing an optical vortex is described by an electric field distribution that may be expressed $E(x, y, z)=A(x, y, z)\exp(i\Phi(x, y, z))\exp(im\theta)$ where A and 90 are arbitrary amplitude and phase functions respectively, $\theta$ is an angle about the vortex core located at $(x_v, y_v)$: $x-x_v=\cos\theta$ and $y-y_v=\sin\theta$, and m is an integer called the vortex charge (or vortex topological charge). There are various techniques to produce convert a given input beam into an output containing an arbitrary distribution of optical vortices. In this example, this method makes use of a space variant half-wave retarder and a circularly polarized input beam. For convenience, the input beam is right circularly polarized.

A conventional half-wave plate converts a right circularly polarized beam into a left circularly polarized beam, without introducing a spatially varying phase on the output beam. This may be accomplished with a birefringent material such as a nematic liquid crystal whereby the refractive index depends on the linear polarization components of the beam.

The horizontal and vertical polarization components of the right circularly polarized input beam may be represented by variable $E_{x,in}=1$ and $E_{y,in}=-i$, where $i=\sqrt{-1}$. In general the output beam has horizontal and vertical components that are a linear combination of the input components. For a half-wave retarder with the fast crystal axis making an angle $\theta'$ with respect to the x-axis, the output field may be expressed $$\begin{bmatrix} E_{x,out} \\ E_{y,out} \end{bmatrix} = \begin{bmatrix} \cos\theta' & -\sin\theta' \\ \sin\theta' & \cos\theta \end{bmatrix} \begin{bmatrix} \exp(i\pi/2) & 0 \\ 0 & \exp(-i\pi/2) \end{bmatrix}$$

$$\begin{bmatrix} \cos\theta' & \sin\theta' \\ -\sin\theta' & \cos\theta \end{bmatrix} \begin{bmatrix} E_{x,in} \\ E_{y,in} \end{bmatrix}$$

When $$\theta' = \frac{\pi}{4},$$

$E_{x,out}=1$ and $E_{y,out}=i$ which describes left circular polarization. The principle of a space-variant half-wave retarder can be understood by re-writing the above equation in the reduced form, making use of the trigonometric identity $\tan(2u)=2\tan u/(1-\tan^2 u)$:

$$\begin{bmatrix} E_{x,out} \\ E_{y,out} \end{bmatrix} = ie^{-i\phi} \begin{bmatrix} 1 \\ i \end{bmatrix}$$

Where $\tan\phi=\tan 2\theta'$, or equivalently, $\phi=2\theta'$. That is, the spatial phase distribution of the output left circularly polarized beam may be controlled by spatially varying the angle of the crystal fast axis. For example, if we want a vortex of charge m=−2 having a spatial phase distribution $\exp(-i2\theta)$. then we need to spatially orient the fast axis of the crystal by the exact angular coordinate $\theta'=\theta$, where $\theta$ corresponds to the (x,y) location of the material: $x=\cos\theta$, $y=\sin\theta$. Likewise, if we want to generate a vortex beam of charge m=−4 then we need to rotate the fast axis by an amount $\theta'=2\theta$.

The half-wave phase factors in the equation above $\exp(\pm i\pi/2)$ may be achieved when the following birefringent material condition is satisfied: $\pi(n_e-n_o)L/\lambda=\pi/2$ where $n_o$ and $n_e$ are the ordinary and extraordinary refractive indexes, respectively, L is the thickness of the material, and $\lambda$ is the wavelength of light. This "half-wave" condition can only be satisfied at a single wavelength. In this case the conversion efficiency (of the right circularly polarized input beam to the left circularly polarized output beam having a vortex phase) decreases as a function of wavelength. To rectify this shortcoming and make the material highly efficient across a band of wavelength, an achromatic half-wave retarder may be used.

Broadband wave retarders may be constructed by stacking multiple layers of the same birefringent material at different orientations. Achromatic and superachromatic wave plates may be constructed from three more layers. A three-layer achromatic half-wave plate is described below. The electric field vector may be described with Jones matrix formalism:

$$\begin{bmatrix} E_{x,out} \\ E_{y,out} \end{bmatrix} = \begin{bmatrix} C_{1,1} & C_{1,2} \\ C_{2,1} & C_{2,2} \end{bmatrix} \begin{bmatrix} B_{1,1} & B_{1,2} \\ B_{2,1} & B_{2,2} \end{bmatrix} \begin{bmatrix} A_{1,1} & A_{1,2} \\ A_{2,1} & A_{2,2} \end{bmatrix} \quad (1)$$

$$\begin{bmatrix} E_{x,in} \\ E_{y,in} \end{bmatrix} = \begin{bmatrix} M_{1,1} & M_{1,2} \\ M_{2,1} & M_{2,2} \end{bmatrix} \begin{bmatrix} E_{x,in} \\ E_{y,in} \end{bmatrix}$$

where $$\begin{bmatrix} A_{1,1} & A_{1,2} \\ A_{2,1} & A_{2,2} \end{bmatrix} = \begin{bmatrix} \cos\theta_a & -\sin\theta_a \\ \sin\theta_a & \cos\theta_a \end{bmatrix} \begin{bmatrix} \exp(i\gamma_a) & 0 \\ 0 & \exp(-i\gamma_a) \end{bmatrix} \quad (2)$$

$$\begin{bmatrix} \cos\theta_a & \sin\theta_a \\ -\sin\theta_a & \cos\theta_a \end{bmatrix}$$

$$\begin{bmatrix} B_{1,1} & B_{1,2} \\ B_{2,1} & B_{2,2} \end{bmatrix} = \begin{bmatrix} \cos\theta_b & -\sin\theta_b \\ \sin\theta_b & \cos\theta_b \end{bmatrix} \begin{bmatrix} \exp(i\gamma_b) & 0 \\ 0 & \exp(-i\gamma_b) \end{bmatrix} \quad (3)$$

$$\begin{bmatrix} \cos\theta_b & \sin\theta_b \\ -\sin\theta_b & \cos\theta_b \end{bmatrix}$$

$$\begin{bmatrix} C_{1,1} & C_{1,2} \\ C_{2,1} & C_{2,2} \end{bmatrix} = \begin{bmatrix} \cos\theta_c & -\sin\theta_c \\ \sin\theta_c & \cos\theta_c \end{bmatrix} \begin{bmatrix} \exp(i\gamma_c) & 0 \\ 0 & \exp(-i\gamma_c) \end{bmatrix} \quad (4)$$

$$\begin{bmatrix} \cos\theta_c & \sin\theta_c \\ -\sin\theta_c & \cos\theta_c \end{bmatrix}$$

Although the ordinary $n_o$ and the extraordinary $n_e$ refractive indexes vary with wavelength, for first order design purposes the birefringence $\Delta n=n_e-n_o$ is often assumed to be nearly constant. (In practice optimization techniques can be used to correct for wavelength-dependent values of $\Delta n$ by varying, for example, the layer thicknesses until the output is sufficiently achromatic.) The wavelength-dependent phase retardance T or a layer of thickness L may be expressed: $2\gamma=\Delta\Phi(\lambda)=2\pi(n_e-n_o)L/\lambda\approx 2\pi L\Delta n(1-\delta\lambda/\lambda)/\lambda_0$ where $\lambda=\lambda_0+\delta\lambda$ and $\lambda_0$ is a central design wavelength for the achromatic retarder.

Figure 9C:
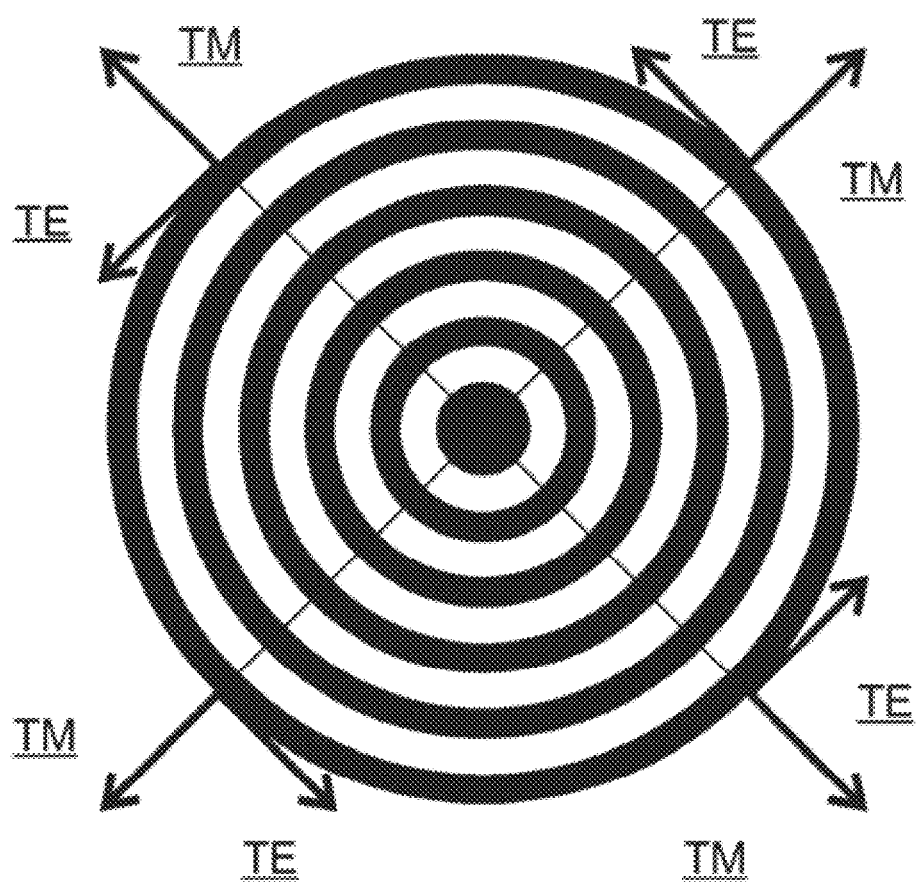
FIG. 9c depicts an example of a vortex mask which can be seen as a polarization FQ-PM.

The waveplate may be achromatized if $\gamma_a=\gamma_c$ and $\theta_a=\theta_c$. In effect, the first and last materials may be the same and the orientations are parallel. The final conditions are that $\cos 2\theta_b=-\gamma_{b,0}/2\gamma_{a,0}$ and $\gamma_{b,0}=\pi/2$. Hence $\cos 2\theta_b=-\pi/4\gamma_{a,0}$ For example:
1. Let $\lambda_0=800$ nm, $\delta\lambda/\lambda_0=0.10$, and $\Delta n=0.15$
2. The condition $\gamma_{b,0}=\pi L_b n/\lambda_0=\pi/2$ is satisfied if $L_b=\lambda_0/2\Delta n=2.67$ μm
3. Let the equal retardances of the first and third layers be an adjustable parameter, or equivalently,
   $L_a=L_c:\gamma_a=\gamma_c=\pi\Delta n L_{a,c}/\lambda$
   The condition $\cos 2\theta_b=\pi/4\gamma_{a,0}$ requires $\theta_b=(\frac{1}{2}) \arccos(-\lambda_0/4\Delta n L_{a,c})$
   For example, if $L_a=L_b=L_c=2.67$ μm, then $\theta_b=\pi/3$
5. Finally we must set $\theta_a=\theta_c$ FIG. 9c depicts an example of a vortex mask which can be seen as a polarization FQ-PM. The parallel potentially interfering polarization states are out of phase according to the FQ-PM focal plane phase shift distribution. φTE and φTM are the output phases of the polarization components TE and TM such that ΔφTE-TM=|φTE-φTM|=π. While some constructions and configurations of AGPMs have been used for astronomy, none have been used for spectroscopy for detection of information in faint signals with significant noise.

The vortex mask 840 may be complemented by a diaphragm in the relayed pupil plane ("Lyot stop") to suppress diffracted light.

Figure 10A:
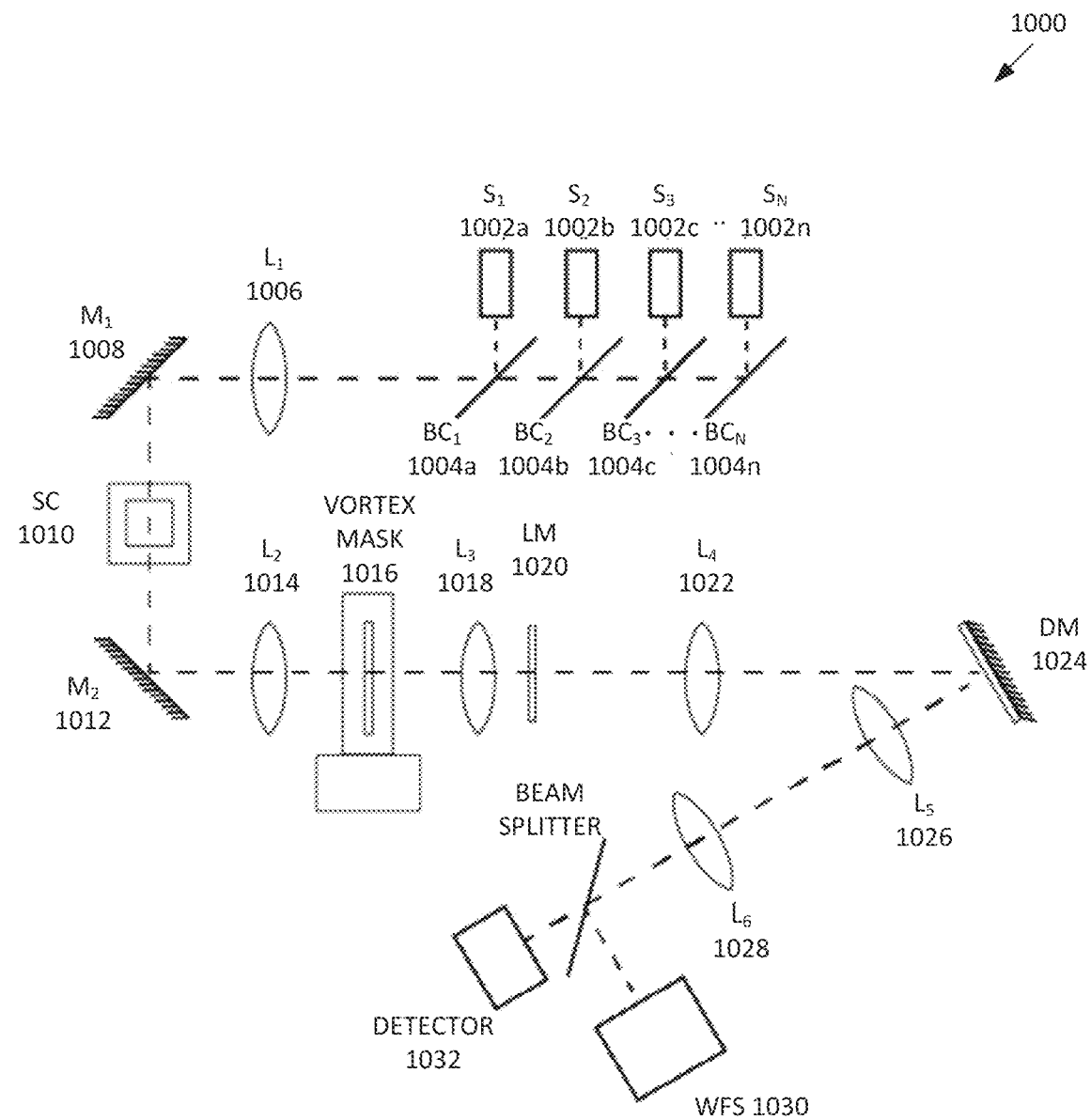
FIG. 10a depicts an example simplified spectrometer optical path in some embodiments.

FIG. 10a depicts an example simplified spectrometer optical path 1000 in some embodiments. One or more light sources may project desired wavelengths along the optical path 1000 through the sample 1010 and then through a vortex mask 1016 to a detector 1032. The vortex mask 1016 may assist with improved signal measurement and signal boosting. As such, measurements of the resulting signal enable a discriminator to detect viruses and/or substances related to viruses (e.g., proteins) to detect infections that were previously too faint to detect.

In various embodiments, the optical path 1000 includes a vortex mask 1016 but not a Lyot mask 1020. In other embodiments, the optical path 1000 includes a vortex mask and a Lyot mask.

Light sources 1002a-n each project light at a different wavelength. In some embodiments, a single laser projects coherent light through a differential grating to separate the wavelengths. In other embodiments, different light sources may project different wavelengths (1002a may be a different wavelength from 1004b and the like). Each Sn may be a different and distinct wavelength as compared to all other sources.

Example wavelengths include, for example, 860 nm, 810 nm, 780 nm, and 735 nm. These wavelengths may, for example, be useful in detecting evidence of COVID-19 infection in a breath sample collected from a patron.

The light sources 1002a-n may be or include five co-boresighted laser sources that create a light source with an 8 mm collimated beam (or other diameter beam may be produced such as 3 mm, 4 mm, 5 mm, 6 mm, 7 mm, 9 mm, or 10 mm for example). Each light source 1002a-n may be or include an FC fiber connected to an achromatic collimator that sets the output beam width. In one example, light sources 1002a-n are diode laser sources of various wavelengths. Collimated light from each light source 1002a-n is reflected from the surface of a 55/45 beam splitter or beam comber ($BC_1$-$BC_N$).

Beam combiners 1004a-1004n each may allow some wavelengths to pass while reflecting at least one wavelength (e.g., combining optical wavelengths). In one example, beam combiner 1004a may reflect light at a first wavelength from source 1002a and the beam combiner 1004a may allow other wavelengths to pass through (e.g., light from sources 1002b-1002n). The light from each source may be projected through lens 1006. Lens 1006 may be a collimator to collimate the light received from the light sources.

Reflective surfaces 1008 and 1012 may reflect all light from the sources. In one example, light from sources 1002a-1002n is reflected by reflective surface 1008 through sample chamber 1010. The sample chamber 1010 may contain a sample (e.g., breath, saliva, or swab sample) from a patron. In various embodiments, the sample chamber 1010 is or contains the cuvette 416. In another example, the sample chamber 1010 is or contains transparent substrates 500. The light from the sources pass through the sample chamber 1010 and is then reflective by reflective surfaces 1012.

The second section of the optical path 1000 propagates the collimated beam through a scattering sample of the sample chamber 1010. In one example, a collimated beam from the light source is reflected perpendicularly from reflective surface M1 1008 through a sample cuvette holder (i.e., the sample chamber 1010). In this example, the entrance aperture of the sample chamber 1010 has a 9 mm diameter. The sample chamber 1010 may contain a sample in a liquid medium and may have a width of 10 mm perpendicular to the beam and a length parallel to the beam of 2 mm.

In one example, the sample chamber 1010 may be filled with approximately 1 ml of liquid so the full 8 mm beam passes through the sample. The residual collimated beam and the light scattered off the sample may then reflected perpendicularly off of reflective surface M2 1012 and exits to the next section of the optical path.

Light is then further focused by lens 1014 on the vortex mask 1016. The lens 1018 may focus the light on the optional Lyot mask 1020 and/or may collimate the light received from the vortex mask 1016.

Optional LM mask 1020 may be a Lyot mask (e.g., Lyot stop) such as a Lyot-plane phase mask, which enables improved contrast performance. The Lyot-plane phase mask may relocate residual light away from a region of the image plane, thereby reducing light noise from the sources of the spectrometer and improving sensitivity to off-axis scattered light.

It may be appreciated that, in some embodiments, the spectrometer includes a vortex mask 1016, a Lyot mask 1020, or both (e.g., the spectrometer may include a Lyot mask 1020 but not a vortex mask 1016, a Lyot mask 1020 and a vortex mask 1016, or vortex mask 1016 but not a Lyot mask 1020).

The lens L4 1022 may collimate the light and/or focus on the light on the optional deformable mirror 1024. In some embodiments, the lens L4 1022 may focus the light on the deformable mirror 1024 (e.g., to a desired diameter).

The deformable mirror 1024 may, in some embodiment, control the wavefront of the light based on information received from the wavefront sensor 1030. In this example, the light may magnify and/or enhance the light of the optical path. Control of the deformable mirror 1024 may allow for control of the wavefront of the light to direct a flat wavefront to the detector 1032. It will be appreciated that, in some examples, the optical path 1000 may not have a deformable mirror 1024. In that case, the optical path 1000 may not have a beam splitter or a wavefront sensor (WFS) 1030.

The detector 1032 detects spectral components (e.g., intensities of received wavelengths). In various embodiments, the detector 1032 is part of a spectrometer, a photodiode, or an LCD camera. The detector may generate measurements indicating intensities of wavelengths from the incoherent light of the optical path. The detector may provide absorption or transmittance measurements related to the particles and components of the breath sample.

In one example, the detector 1032 is in communication with a processor to assess and generate the measurement results. The measurement results may then be used to identify if the patron that produced the breath sample is infected.

The measurement results may be received by a discriminator. A discriminator may categorize or determine if the patron is infected by assessing and/or analyzing the measurement results. The discriminator may assess the measurement results using a logistic regression technique, an AI approach (e.g., convolutional neural network), and/or other statistical methods. In some embodiments, the measurement results may be used to create and/or train the discriminator.

In various embodiments, there is a beam splitter in the optical path before the detector thereby enabling the beam to be split between the detector 1032 and the wavefront sensor (WFS) 1030. A wavefront sensor 1030 is a device for measuring aberrations in an optical wavefront (e.g., points where the wave has the same phase as the sinusoid) and controlling the deformable mirror 1024 to correct and flatten the optical wavefront.

Lens 5 1026 and lens 6 1028 may also focus and collimate the light to project to the wavefront sensor 1030 and/or detector 1032.

Figure 10B:
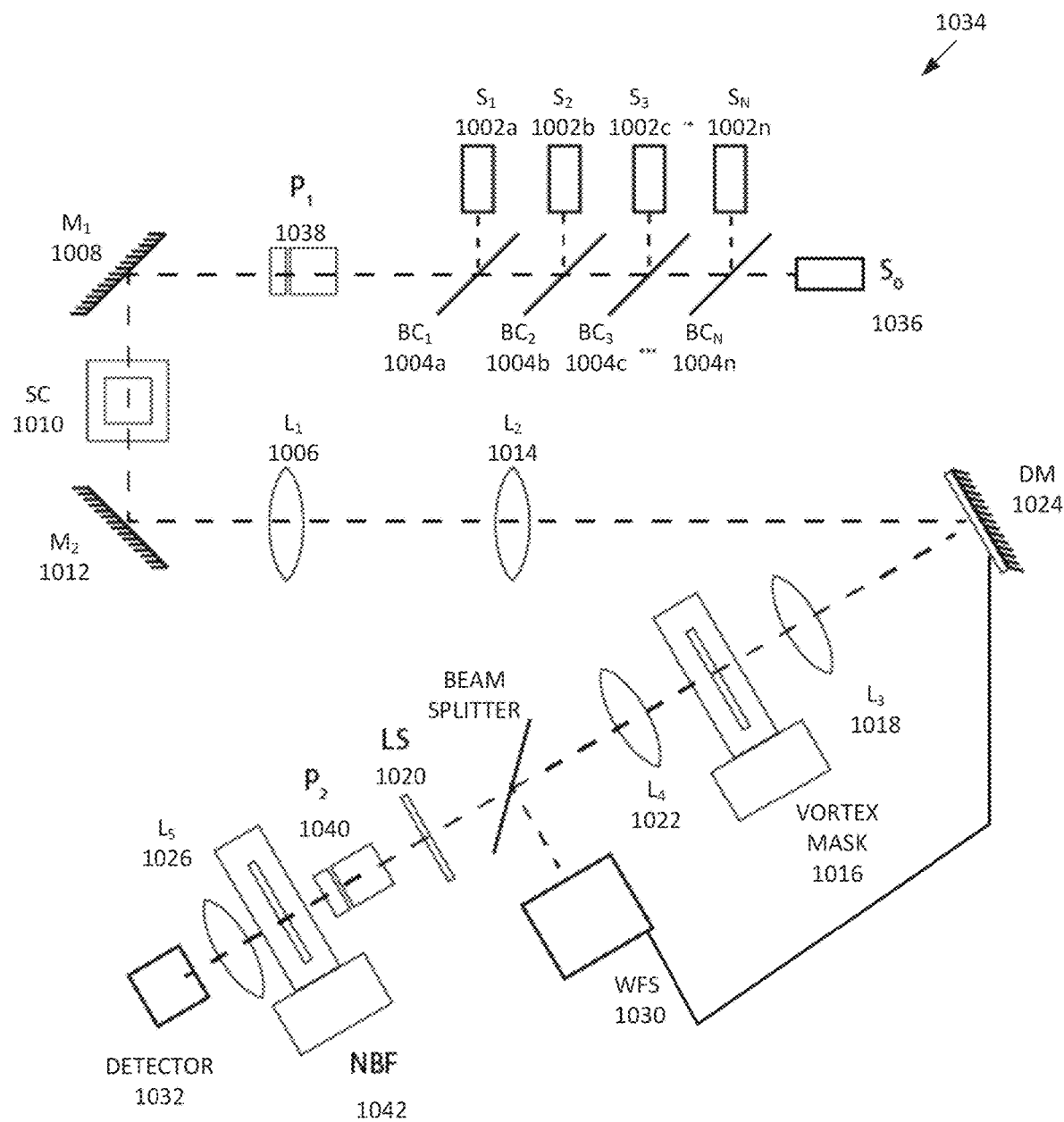
FIG. 10b depicts another example simplified spectrometer optical path in some embodiments.

FIG. 10b depicts another example simplified spectrometer optical path 1034 in some embodiments. Similar to FIG.

10a, the light sources 1036 and 1002a-n project desired wavelengths along the optical path 1034 through the sample 1010 and then through a vortex mask 1016 to a detector 1032. The vortex mask 1016 may assist with improved signal measurement and signal boosting. As such, measurements of the resulting signal enable a discriminator to detect viruses and/or substances related to viruses (e.g., proteins) to detect infections that were previously too faint to detect. In this example, different from FIG. 10a, the vortex mask 1016 and the optional Lyot stop 1020 has been moved to after the deformable mirror 1024.

Figures 11A, 11B:
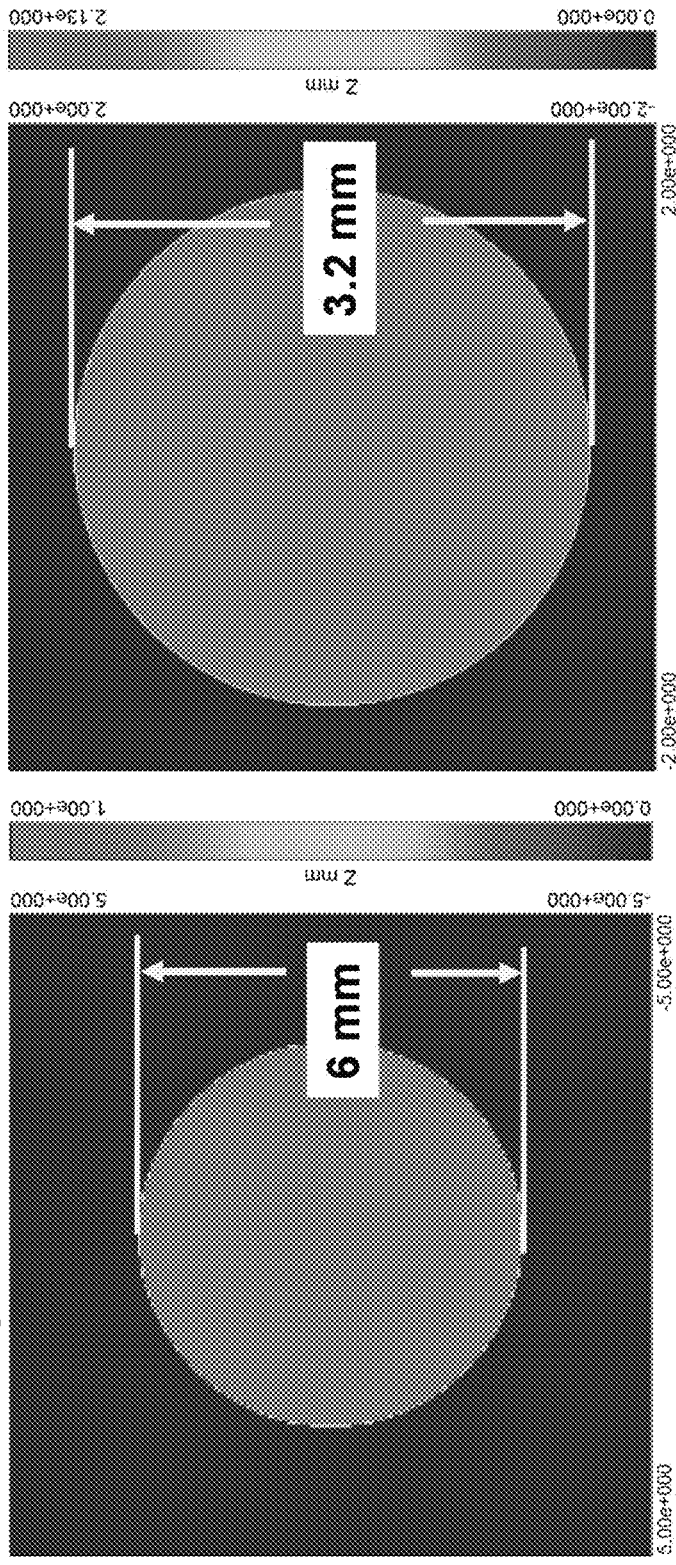
FIG. 11a depicts a measurement of the aperture of an entrance aperture as being 6 mm in one example.
FIG. 11b depicts a measurement of an optical beam received and reflected by a deformable mirror in some embodiments.

In various embodiments (e.g., in any spectrometer discussed herein), the beam size may be narrowed to ensure that the beam passes through the cuvette and not clip a corner or edge of the cuvette. The beam sized may be 4 mm from the light source (e.g., at the entrance aperture) for example. Other examples of the beam size may be 4 mm to 8 mm. The lens from M2 1012 may be reduced to 3.2 mm on the deformable mirror 1024. Other examples of the beam size may be 3 mm to 4 mm. In some embodiments, lens 1006 and 1014 reduce the beam to the deformable mirror 1024. FIG. 11a depicts a measurement of the aperture of an entrance aperture as being 6 mm in one example. In this example, the aperture accommodates an optical beam with a 6 mm diameter. FIG. 11b depicts a measurement of an optical beam received and reflected by a deformable mirror in some embodiments. In this example, the deformable mirror accommodates an optical beam of a 3.2 mm diameter received from one or more lenses along the optical path 1034.

In various embodiments, the optical path 1034 includes a vortex mask 1016 but not a Lyot mask 1020. In other embodiments, the optical path 1034 includes a vortex mask 1016 and a Lyot mask 1020.

Light sources 1036 and 1002a-n each project light at a different wavelength. In some embodiments, a laser projects coherent light through a differential grating to separate the wavelengths. In other embodiments, different light sources may project different wavelengths (1002a may be a different wavelength from 1002b and the like). Each Sn may be a different and distinct wavelength as compared to all other sources.

Example wavelengths include, for example, 860 nm, 810 nm, 780 nm, and 735 nm. These wavelengths may, for example, be useful in detecting evidence of COVID-19 infection in a breath sample collected from a patron.

The light sources 1036 and 1002a-n may be or include five co-bore-sighted laser sources that create a light source with an 8 mm collimated beam. The light source S0 1036 may be a control wavelength. In some embodiments, the light source S0 1036 is 635 nm.

The light sources 1002a-n and/or the light source 1036 may be or include five co-bore-sighted laser sources that create a light source with an 8 mm collimated beam. Each light source 1036 and 1002a-n may be or include an FC fiber connected to an achromatic collimator that sets the output beam width to 8 mm. In one example, light sources 1036 and 1002a-n are diode laser sources of various wavelengths. Collimated light from each light source 1036 and 1002a-n is reflected from the surface of a 55/45 beam splitter or beam comber ($BC_1$-$BC_N$).

In some embodiments, the spectrometer may include a white light source. In this configuration, the FC connected fiber from a laser diode source Si is replaced with a fiber fed light source from a tungsten halogen bulb projecting white light.

Beam combiners 1004a-1004n each may allow some wavelengths to pass while reflecting at least one wavelength (e.g., combining optical wavelengths). In one example, beam combiner 1004a may reflect light at a first wavelength from source 1002a and the beam combiner 1004a may allow other wavelengths to pass through (e.g., light from sources 1002b-1002n). The light from each source may be projected through lens 1006a. Lens 1006a may be a collimator to collimate the light received from the light sources.

Reflective surfaces 1008 and 1012 may reflect all light from the sources. In one example, light from sources 1002a-1002n is reflected by reflective surface 1008 through sample chamber 1010. The sample chamber 1010 may contain the breath sample, saliva, or other sample from a patron. In various embodiments, the sample chamber 1010 is or contains the cuvette 416. In another example, the sample chamber 1010 is or contains transparent substrates 500. The light from the sources pass through the sample chamber 1010 and is then reflected by reflective surfaces 1012.

The second section of the optical path 1034 propagates the collimated beam through a scattering sample of the sample chamber 1010. In one example, an 8 mm collimated beam from the light source is reflected perpendicularly from reflective surface M1 1008 through a sample cuvette holder (i.e., the sample chamber 1010). In this example, the entrance aperture of the sample chamber 1010 has a 9 mm diameter. The sample chamber 1010 may contain a sample in a liquid medium and may have a width of 10 mm perpendicular to the beam and a length parallel to the beam of 2 mm.

In one example, the sample chamber 1010 may be filled with approximately 1 ml of liquid so the full 8 mm beam passes through the sample. The residual collimated beam and the light scattered off the sample may then reflected perpendicularly off of reflective surface M2 1012 and exits to the next section of the optical path.

Lens 1006 may collimate the light and L2 1014 may focus the light on the deformable mirror 1024. Collimated light from the sample chamber 1010 may be incident on lens L1 1006. Lenses L1 (e.g., f1=75 mm) and L2 (e.g., f2=30 mm) may be separated by a distance D12=f1+f2=105 mm. In this example, the light leaving lens L2 1014 is collimated with a beam size of 3.2 mm. The collimated beam is incident on a BMC MEMS deformable mirror 1024 composed of, in this example, an equal spaced, 12×12 actuator grid array, where each actuator is separated by 400 microns.

The deformable mirror 1024 may, in some embodiment, control the wavefront of the light based on information received from the wavefront sensor 1030. In this example, the light may magnify and/or enhance the light of the optical path. Control of the deformable mirror 1024 may allow for control of the wavefront of the light to direct a flat wavefront to the detector 1032. It will be appreciated that, in some examples, the optical path 1000 may not have a deformable mirror 1024. In that case, the optical path 1000 may not have a beam splitter or a wavefront sensor WFS 1030.

Light then is further focused by lens 1018 on the vortex mask 1016. The vortex coronagraph 1016 may be created by first constructing a 4f beam relay using 2 matching 75 mm lenses, L3 (f3=75 mm) and L4 (f4=75 mm). Lens L3 1018 may be placed a distance equal to the focal length of lens L3 away from the DM (D3=75 mm). Lens L3 1018 and L4 1022 may be separated by a distance D34=f3+f4=150 mm.

In some embodiments, a collection of monochromatic vortex masks (VM) matched to the input laser diodes are loaded into a filter wheel and placed in the focal plane between L3 1018 and L4 1022. The filter wheel may be mounted to a 3-axis translation stage to provide fine position control for vortex mask alignment. In various embodiments (e.g., any of examples depicted in FIGS. 10a-c), the irradiance at the entrance of the vortex mask may be 34 micrometers.

Lens L4 1022 may be a collimator lens and/or may focus the light on the Lyot stop 1020. In this example, a Lyot stop (LS) 1020 is place after lens L4 1022 at a distance of D4=75 mm. Different Lyot stop 1020 sizes may be used. In one example, a Lyot stop 1020 uses a 0.8×Dpupil≅2.56 mm aperture.

The Lyot stop 1020 may be a Lyot-mask (e.g., Lyot stop) such as a Lyot-plane phase mask, which enables improved contrast performance. The Lyot-plane phase mask may relocate residual light away from a region of the image plane, thereby reducing light noise from the sources of the spectrometer and improving sensitivity to off-axis scattered light.

In between lens L4 1022 and the Lyot Stop (LS) 1020 a 92/8 beam splitter (BS) is placed in the beam, the 8% reflection is passed into a Shack-Hartmann wavefront sensor (WFS) 1030 which is also a distance D4=75 mm after lens L4 1022.

The WFS 1030 may measure the wavefront of the light and control the deformable mirror to flatten the wavefront on the vortex mask 1016 (otherwise signature artifacts may be created).

It may be appreciated that the system may be configured for broadband use by replacing the monochromatic vortex masks with broadband masks that are matched to the new set of narrowband filters in the detector optics.

The residual light that exits the Lyot stop 1020 is passed through a circular polarization analyzer (P2) 1040 that is matched to the circular polarizer 1038 in the light source system. The light may then be passed through a Filter wheel with 10 nm narrowband pass filters (NBF) 1042 which may have central wavelengths that are matched to the laser diode sources. The residual light may then be focused onto a detector by lens L5 1026 (e.g., f5=7.5 mm). It may be appreciated that the high contrast (>104) performance of the light suppression will be limited by the polarization purity of the beam, so care may be taken to maximize polarization purity.

In some embodiments, a linear array may be used if white light is instead used. In this case the detector is replaced with a fiber mounted multi-mode fiber with a fiber core size greater than 10 microns (Typical use is 400 microns). When setup in the white light configuration, the narrowband filters may be setup to have the same bandpass as the broadband.

The detector 1032 detects spectral components (e.g., intensities of received wavelengths). In various embodiments, the detector 1032 is part of a spectrometer, a photodiode, or an LCD camera. The detector may generate measurements indicating intensities of wavelengths from the incoherent light of the optical path. The detector may provide absorption or transmittance measurements related to the particles and components of the breath sample.

In one example, the detector 1032 is in communication with a processor to assess and generate the measurement results. The measurement results may then be used to identify if the patron that produced the breath sample is infected.

The measurement results may be received by a discriminator. A discriminator may categorize or determine if the patron is infected by assessing and/or analyzing the measurement results. The discriminator may assess the measurement results using a logistic regression technique, an AI approach (e.g., convolutional neural network), and/or other statistical methods. In some embodiments, the measurement results may be used to create and/or train the discriminator.

FIG. 10c is another example of an optical path of a spectrometer in some embodiments. In the example described with reference to FIG. 10c, each component will include a location measured directly to the previous component along the optical path (in the direction against incoming light) and another location measured directly along the optical path to the entrance aperture (e.g., the detector may be 1239.257 mm along the optical path from the entrance aperture 1050). These locations are by way of example. It will be appreciated that the components may be located in many different positions relative to each other, the entrance aperture, and/or the light source.

The path may include an entrance aperture 1050. The entrance aperture 1050 may have a beam aperture. For example, the entrance aperture 1050 may accommodate a beam diameter of 6 mm for a beam of wavelength 635 nm. It may be appreciated that the entrance aperture 1050 may accommodate a beam diameter of any size (e.g., between 4-8 mm) and at any wavelength (e.g., 592 nm-700 nm). The entrance aperture 1050 may be any distance from the light source (e.g., 30 mm).

The polarizer 1052 may be made of any material, such as calcite. The polarizer 1052 may be 63.9463 mm from the light source and 30 mm along the light path to the entrance aperture 1050. The polarizer 1052 may polarize light from the light source received via the entrance aperture 1050.

The quarter wave plate (QWP) 1054 may reflect light received from the polarizer 1052 to the cuvette 1056. The quarter wave plate 1054 may be 99.978 mm from the polarizer 1052 and 93.9463 from the entrance aperture 1050.

The cuvette 1056 may contain a sample from a patient or user that is to be measured. The cuvette may be located 124.1297 mm from the quarter wave plate 1054 and 193.9243 mm from the entrance aperture 1050.

The quarter wave plate 1058 may receive light received through the cuvette 1056 and may reflect all or part of the light to lens 1060.

Lens 1060 may receive light from the quarter wave plate 1058 and allow the light to pass to the lens 1062. The lens 1060 may include, for example, a first side surface radius of curvature 108.07 mm and the other surface (the second side) may be plano. In this example, the lens 1060 may have a thickness of 10 mm and be made of a material such as N—Bk7. It will be appreciated that the surface radius of curvature may be many different sizes (e.g., 90 mm to 120 mm), the other surface may be plano or curved, the lens 1060 may have any different thickness (e.g., 8-12 mm), and be made of any material or combination of materials. The lens 1060 may be 318.28 mm from the cuvette 1056 or the quarter wave plate 1058. The lens 1060 may be 318.054 from the entrance aperture 1050.

Lens 1062 may receive light from the lens 1060 and allow the light to pass to the deformable mirror 1064. The lens 1062 may include, for example, a first side being plano and a second side having a surface radius of curvature −57.64 mm. In this example, the lens 1062 may have a thickness of 10 mm and be made of a material such as N—Bk7. It will be appreciated that the surface radius of curvature may be many different sizes (e.g., −45 mm to −75 mm), the other surface may be plano or curved, the lens 1062 may have any different thickness (e.g., 8-12 mm), and be made of any material or combination of materials. The lens 1062 may be 93.9994 mm from the lens 1060. The lens 1062 may be 636.582 mm from the entrance aperture 1050.

Deformable mirror 1064 may receive light from the lens 1062 and project the light to the lens 1066. The deformable mirror 1064 may be 78.834 mm from the lens 1062 and may be 760.5814 mm from the entrance aperture 1050.

Lens 1066 may receive light from the deformable mirror 1064 and allow the light to pass to the vortex mask 1068. The lens 1066 may include, for example, a first side having a surface radius of curvature 38.6 mm and a second side being plano. In this example, the lens 1066 may have a thickness of 10 mm and be made of a material such as N—Bk7. It will be appreciated that the surface radius of curvature may be many different sizes (e.g., 25 mm to 55 mm), the other surface may be plano or curved, the lens 1066 may have any different thickness (e.g., 8-12 mm), and be made of any material or combination of materials. The lens 1066 may be 76.3095 mm from deformable mirror 1064. The lens 1066 may be 805.4154 mm from the entrance aperture 1050.

Figure 12:
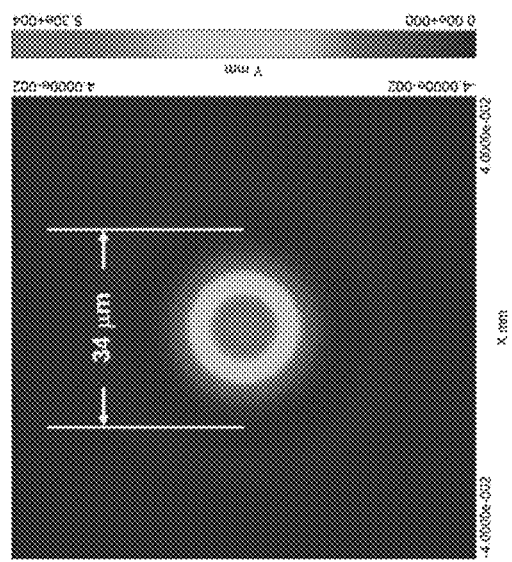
FIG. 12 depicts the irradiance at the entrance to the vortex mask is 34 micrometers in one example.

The vortex mask 1068 may receive light from the lens 1066 and allow (at least some) of the light to pass to lens 1070. The vortex mask 1068 may be 72.0435 mm from the lens 1066 and may be 881.7249 mm from the entrance aperture 1050. FIG. 12 depicts the irradiance at the entrance to the vortex mask 1068 is 34 micrometers in one example.

Figure 13B:
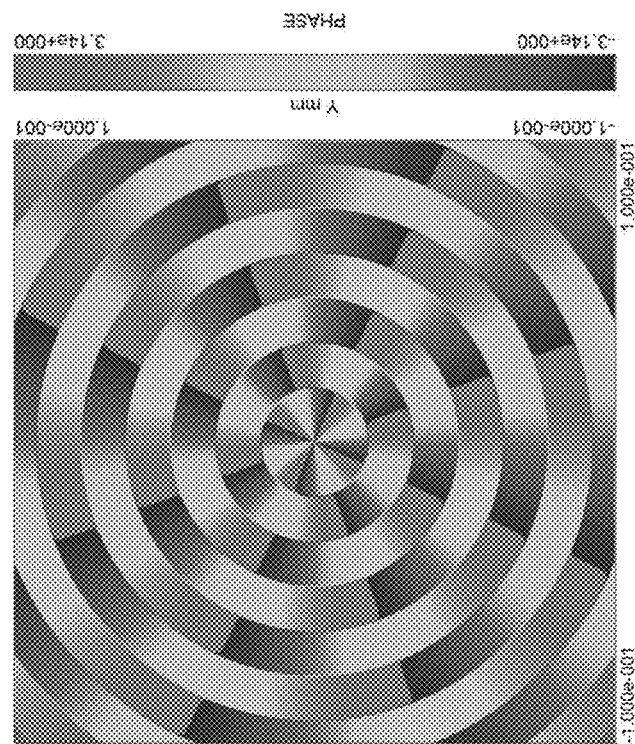
FIG. 13b depicts a field phase (radians) after the vortex mask in some embodiments.
Figure 13A:
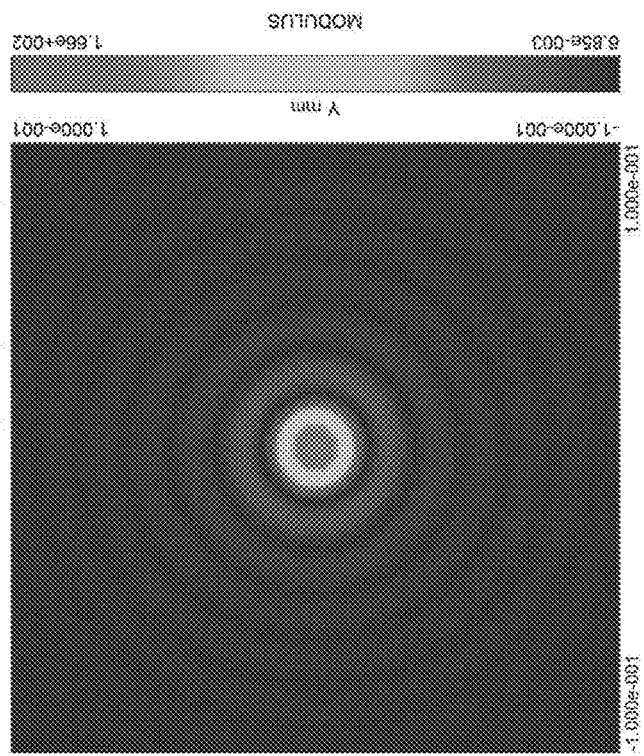
FIG. 13a depicts a field modulus (amplitude) after the vortex mask in some embodiments.

FIGS. 13*a* and 13*b* depict modulus and phase, respectively, of the field after the vortex mask 1068 in some embodiments. FIG. 13*a* depicts a field modulus (amplitude) after the vortex mask 1068 in some embodiments. FIG. 13*b* depicts a field phase (radians) after the vortex mask 1068 in some embodiments.

Lens 1070 may receive light from the vortex mask 1068 and allow the light to pass to the Lyot stop 1072. The lens 1070 may include, for example, a first side being plano and a second side having a surface radius of curvature −38.6 mm. In this example, the lens 1068 may have a thickness of 10 mm and be made of a material such as N—Bk7. It will be appreciated that the surface radius of curvature may be many different sizes (e.g., −30 mm to −45 mm), the other surface may be plano or curved, the lens 1070 may have any different thickness (e.g., 8-12 mm), and be made of any material or combination of materials. The lens 1070 may be 78.934 mm from the vortex mask 1068. The lens 1070 may be 953.7684 mm from the entrance aperture 1050.

The Lyot stop 1072 may receive light from the lens 1070 and allow (at least some) of the light to pass to beam splitter 1074. The Lyot stop 1072 may be 57.1156 mm from the lens 1070 and may be 1,032.702 mm from the entrance aperture 1050.

Figures 14A, 14B:
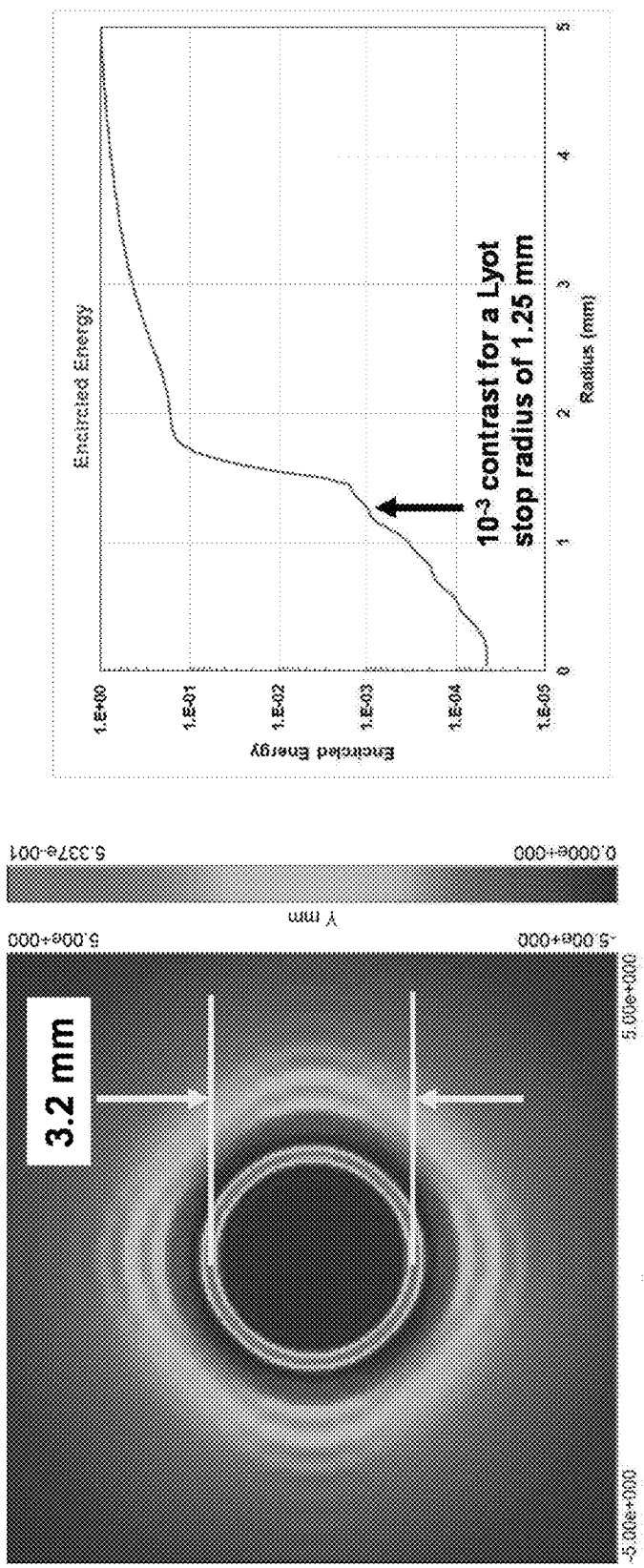
FIG. 14a depicts an example interior irradiance of the Lyot stop in one example.
FIG. 14b is a graph indicating a $10^{-3}$ contrast for a Lyot stop radius of 1.25 mm in one example.

FIGS. 14*a* and 14*b* depict interior irradiance at the Lyot stop 1072 in some embodiments. The vortex mask 1068 may produce a "ring of fire" at the Lyot stop plane. The interior irradiance may be approximately $10^{-4}$ of the ring irradiance and the total power may be, for example, 9.33. FIG. 14*a* depicts an example interior irradiance of the Lyot stop 1072 in one example. FIG. 14*b* is a graph indicating a $10^{-3}$ contrast for a Lyot stop radius of 1.25 mm in one example.

The beam splitter 1074 may receive light from Lyot stop 1072 and allow (at least some) of the light to pass to polarizer 1076. The beam splitter 1074 may be 68.7634 mm from the Lyot stop 1072 and may be 1,089.818 mm from the entrance aperture 1050. The beam splitter 1074 may be configured to measure all or some of the received light, compare the characteristics to criteria or a reference, and control the deformable mirror 1064 to control the light beam.

The polarizer 1076 may receive light from beam splitter 1074 and allow the light to pass to lens 1078. The polarizer 1076 may be 50 mm from the beam splitter 1074 and may be 1,180.581 mm from the entrance aperture 1050.

Lens 1078 may receive light from the polarizer 1076 and allow the light to pass to the detector 1080. The lens 1078 may include, for example, a first side having a surface radius of curvature 8.89 mm and a conic constant of −0.717. The second side may be plano. In this example, the lens 1078 may have a thickness of 2.5 mm and be made of a material such as N—SF11. It will be appreciated that the surface radius of curvature may be many different sizes (e.g., 2-15 mm), the other surface may be plano or curved, the lens 1078 may have any different thickness (e.g., 1-5 mm), and be made of any material or combination of materials. The lens 1078 may be 8.676 mm from the polarizer 1076. The lens 1078 may be 1,230.581 mm from the entrance aperture 1050.

The detector 1080 may receive light from the lens 1078. The detector may be or include a camera such as a CCD. In this example, the detector 1080 may be 1,239.257 mm from the entrance aperture 1050.

Figure 15:
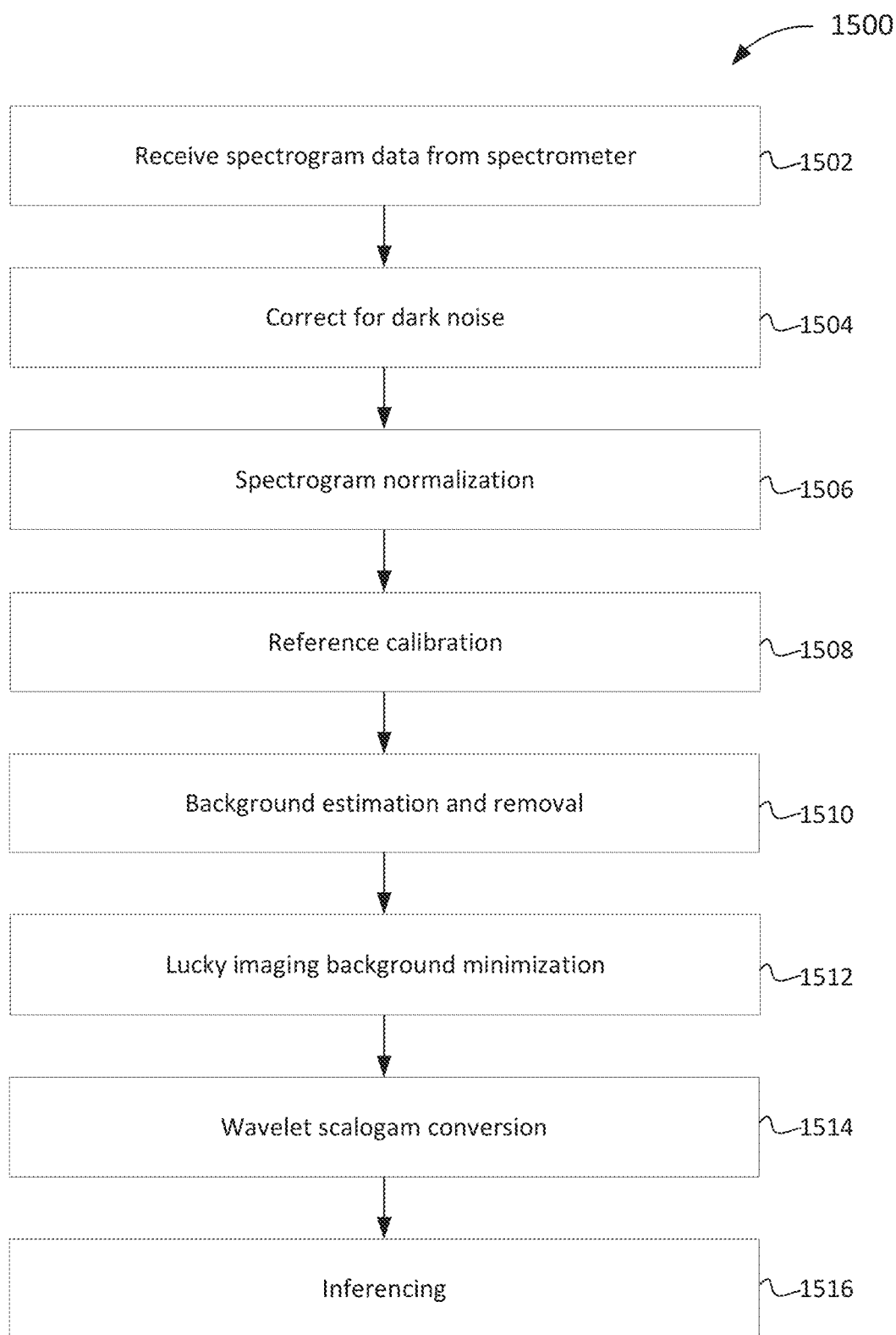
FIG. 15 is a flowchart for identifying infection from spectrometer data in some embodiments.

FIG. 15 is a flowchart for identifying infection from spectrometer data in some embodiments. In some embodiments, a spectrometer as discussed herein may take measurements of a patient's sample (e.g., saliva, breath, or the like). The measurements may then be analyzed to detect infection. Different viruses may produce different wavelength intensities. As a result, a virus may be associated with a "signature" or "thumbprint" of spectral intensities that may be detected.

In step 1502, a digital device may receive spectrogram data from a spectrometer as discussed herein (e.g., with or without a vortex spectrometer and Lyot stop, including, for example, the spectrometer depicted in FIG. 10*a*, 10*b*, or 10*c*). The digital device may be local or remote to the spectrometer that produced the spectrometer results. In one example, the spectrometer may be a health screening system as discussed herein. The digital device may receive raw spectrogram data or spectrogram data after transmission and reconstruction.

In step 1504, the digital device may perform dark noise correction. Dark noise arises from changes in thermal energy of the spectrometer and/or camera (e.g., detector). The increase of signal also carries a statistical fluctuation known as dark current noise.

Measurements of dark noise may be made using digital numbers. Digital numbers are assigned to a pixel in the form of a binary integer, often in the range of 0-255 (a byte). A single pixel may have several digital number variables corresponding to different bands recorded.

Figure 16A:
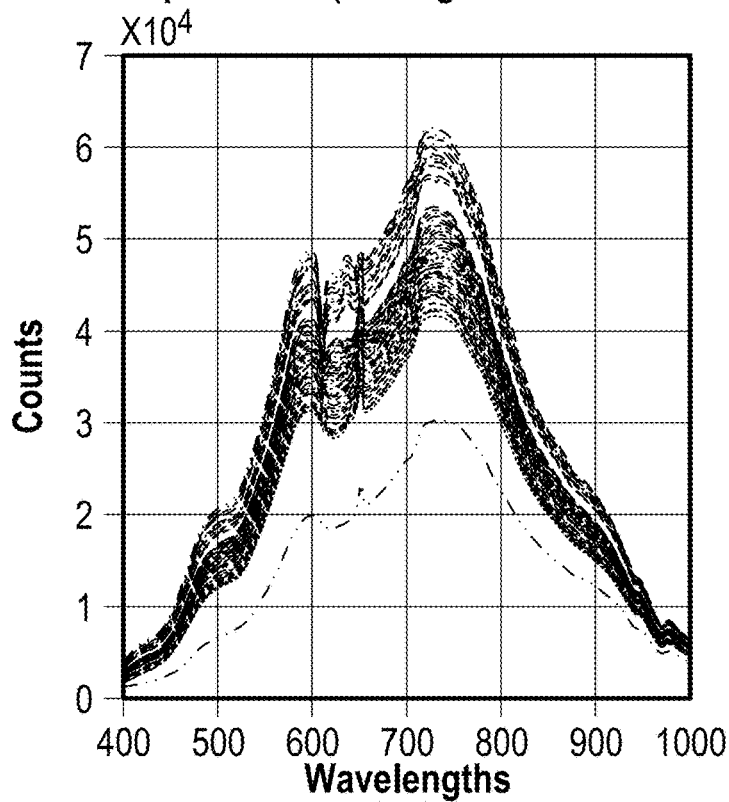
FIG. 16a depicts a test spectra in one example.
Figure 16B:
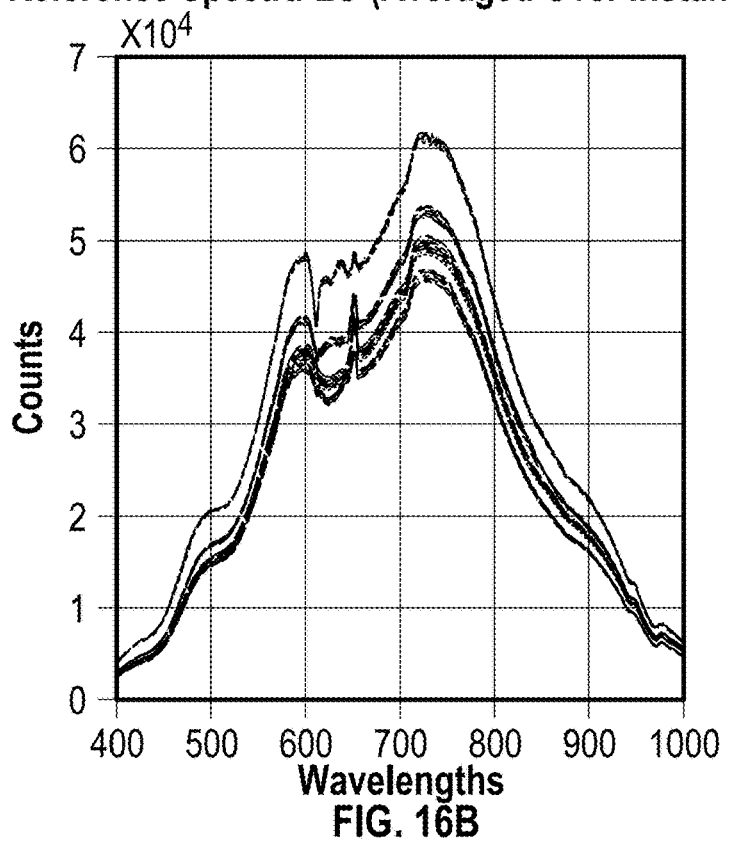
FIG. 16b depicts a reference spectra in one example.
Figure 16C:
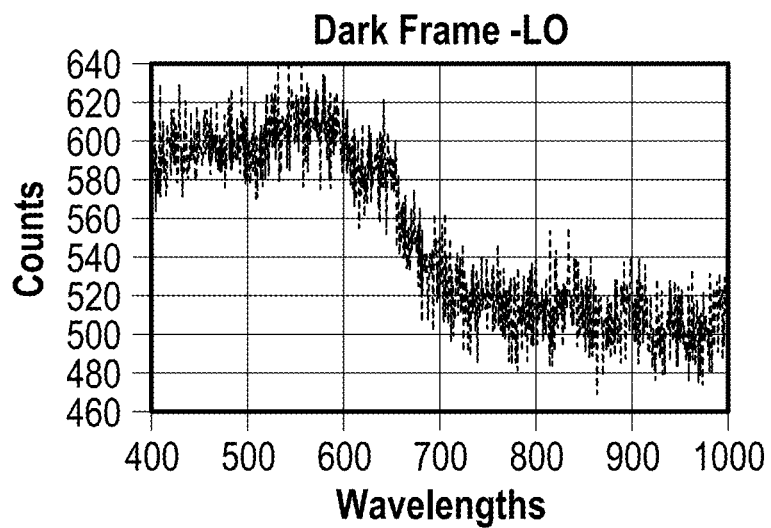
FIG. 16c depicts the mean value of the dark noise in one example.

FIG. 16*a* depicts a test spectra and FIG. 16*b* depicts a reference spectra in two examples. Here, the shape of the spectra is observed, and the signal may be, in this example, about 60,000 digital numbers. The resulting dark noise in comparing the reference to the test has a mean value of about 600 digital numbers. FIG. 16*c* depicts the mean value of the dark noise in one example.

It will be appreciated that the dark noise for a particular spectrometer may not change. As a result, the spectrometer may be tested in a factory to identify dark noise and then a dark noise correction may be applied to spectrogram data throughout the day or going forward. In some embodiments, the spectrometer may be tested daily or at some other periods of time, and then the dark noise detected during testing may be used to correct spectrogram data.

In various embodiments, the dark noise caused by the spectrometer may be filtered from the data. By identifying dark noise and filtering the dark noise from the spectrometer data, the signal (e.g., meaningful spectral intensities) may be boosted.

In various embodiments, the dark noise of a particular spectrometer may be measured. This may be done by letting the spectrometer warm up and measuring water and/or a common transport medium. Noise caused by thermal changes may be detected by the detector (e.g., by a CCD camera). Multiple measurements may be taken (e.g., at the same time or over time) and the dark noise may be averaged, aggregated, and/or otherwise collected.

Figure 16D:
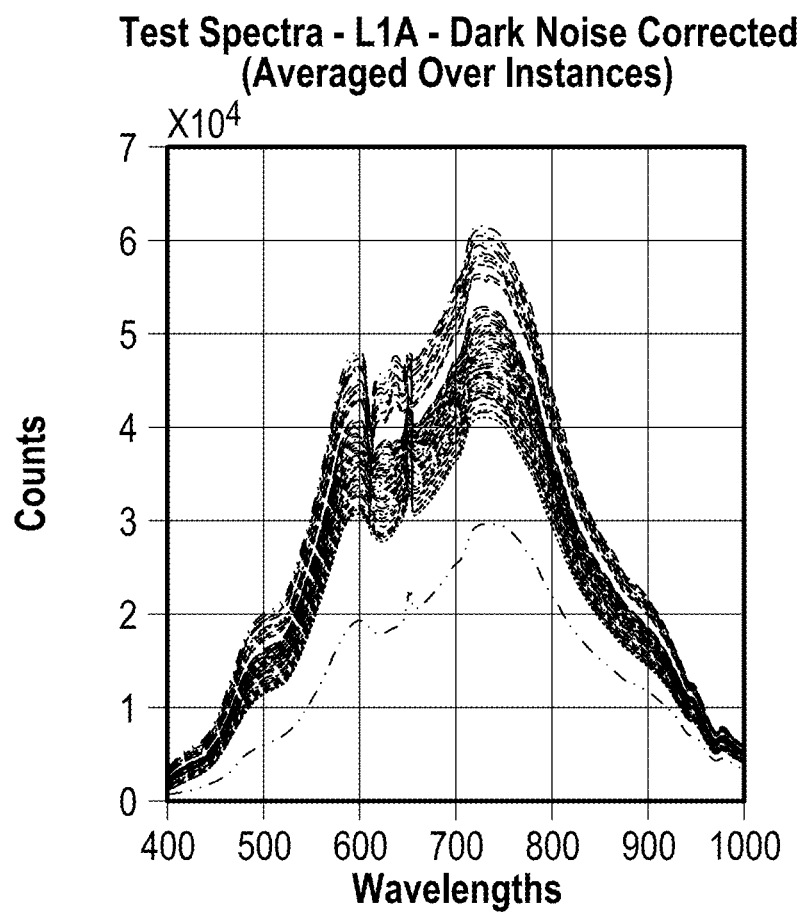
FIG. 16d depicts a test spectra for dark noise corrected in one example.
Figure 16E:
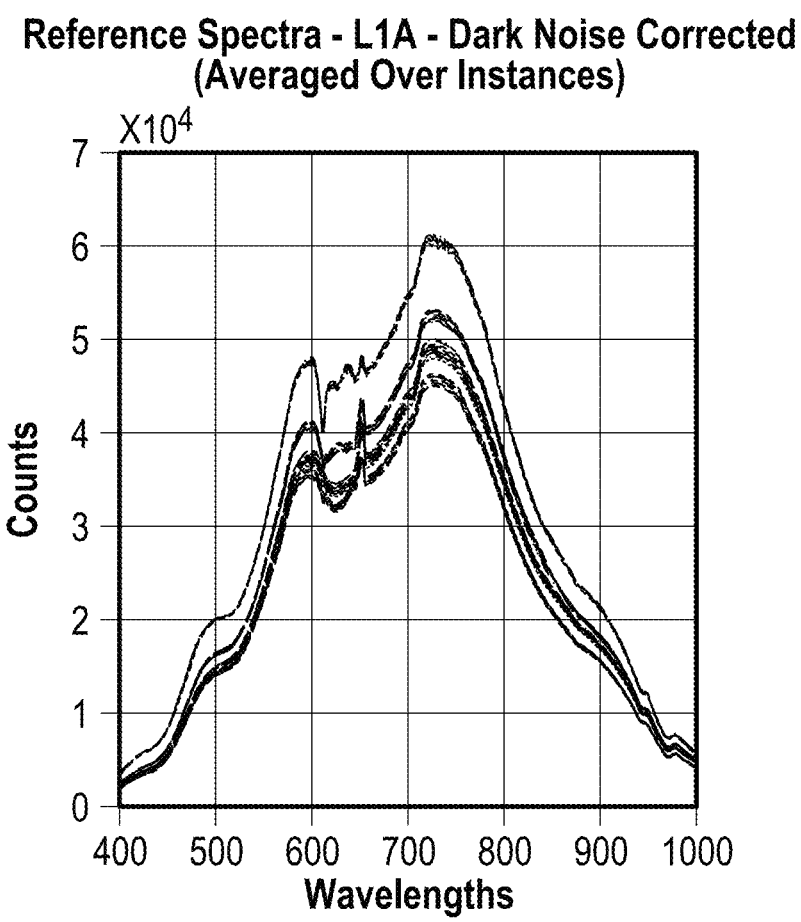
FIG. 16e depicts a reference spectra for dark noise corrected in one example.

FIG. 16d depicts a test spectra corrected for dark noise in one example. FIG. 16e depicts a reference spectra for dark noise in one example.

In step 1506, the digital device performs spectrogram normalization. Variations from sample to sample may create issues. In some embodiments, an autoexposure is used. For example, the digital device and/or the spectrometer may take an image of the spectral intensities and determine location in a fixed integration of time and determine the integration time to get to a desired measurement (e.g., 60,000 digital numbers).

In some embodiments, reference data may be taken (e.g., by using the spectrometer on water or VTM) and a location of a peak intensity identified. The digital device may scale the spectral intensities from that wavelength. The reference information may be taken using water or a VTM to determine peak intensity. The reference may be taken at the factory, once a day, or at any time.

This correction may assist flat fielding of the CCD camera where some pixels are not as sensitive as other pixels in the CCD camera (which as a result, may detect information that is not caused by differences in intensity but rather differences in chip sensitivities).

For example, a determination of where a peak occurs in the reference may be performed. Then all references may be scaled to that peak intensity.

Figure 17A:
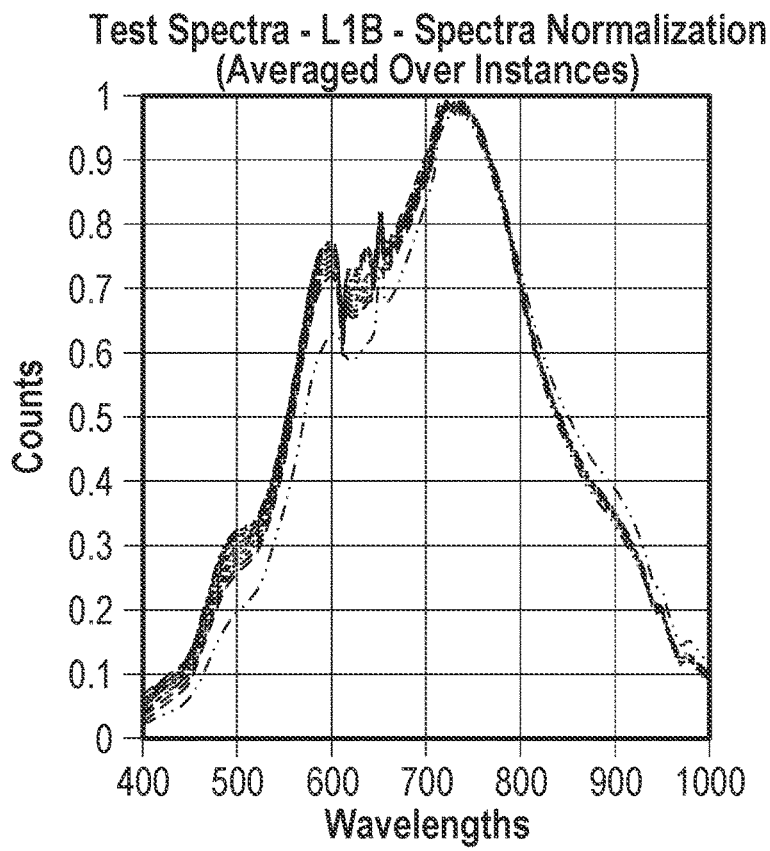
FIG. 17a depicts an example test spectra including spectra normalization averaged over instances.
Figure 17B:
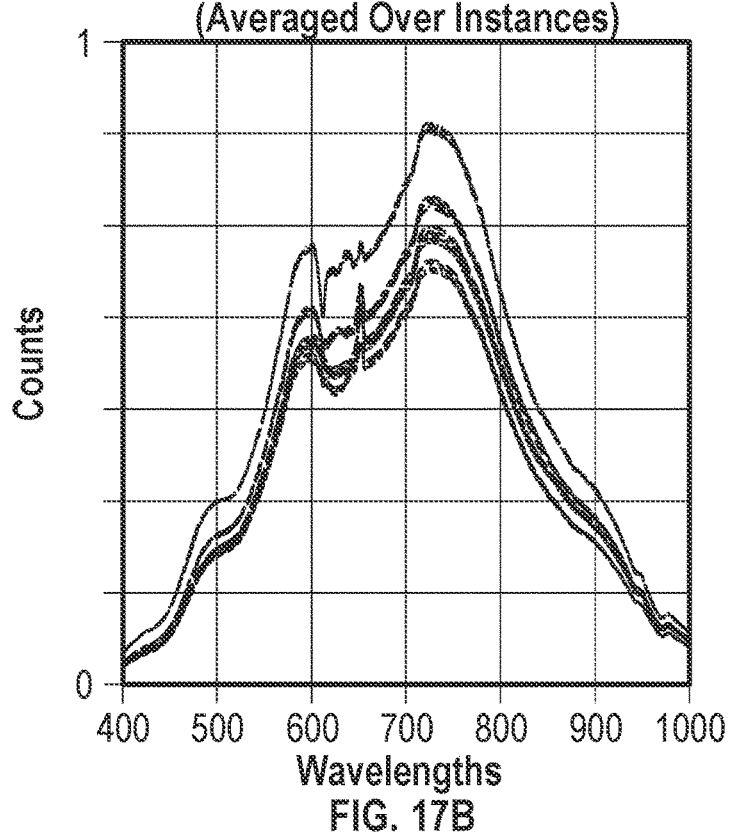
FIG. 17b depicts an example reference spectra including spectra normalization averaged over instances.

FIG. 17a depicts an example test spectra including spectra normalization averaged over instances. FIG. 17b depicts an example reference spectra including spectra normalization averaged over instances.

Figure 17C:
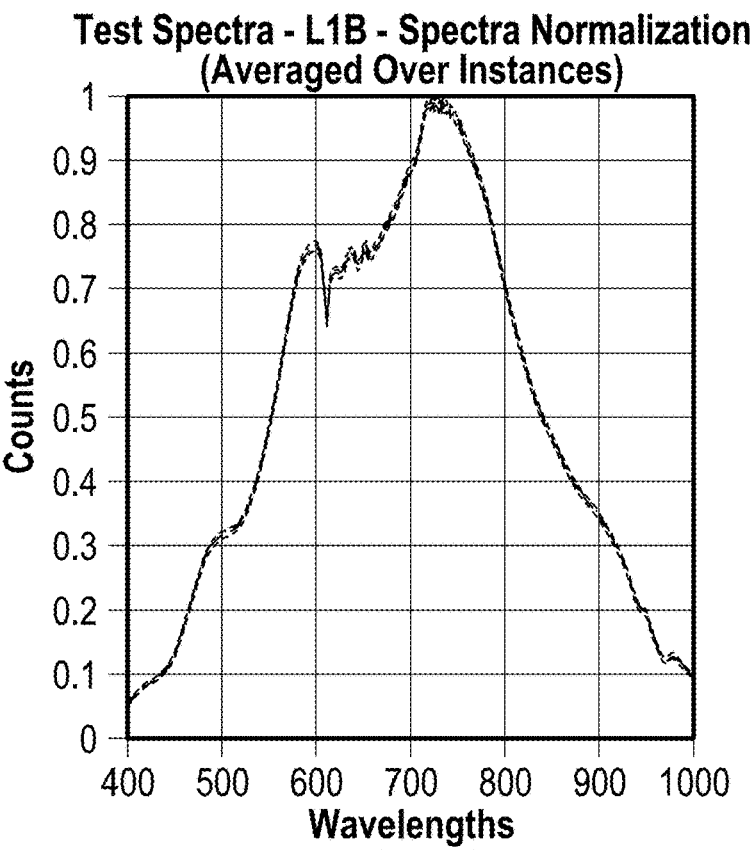
FIG. 17c depicts a test spectra with spectra normalization for the first sample, all instances.
Figure 17D:
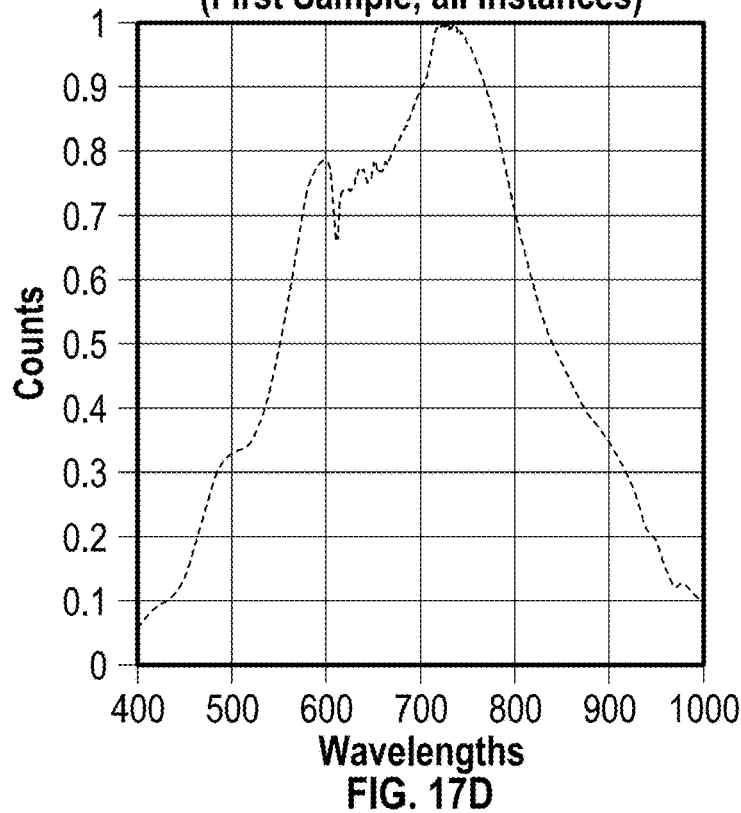
FIG. 17d depicts an example reference spectra including spectra normalization for the first sample, all instances.

FIG. 17c depicts a test spectra with spectra normalization for the first sample, all instances. FIG. 17d depicts an example reference spectra including spectra normalization for the first sample, all instances.

In step 1508, the digital device performs reference calibration. In one example, the digital device takes the ratio of the reference to the signal and then subtracts the reference. The curve may be characteristic of the substance. A flat line would indicate no information.

$$\text{Signal} = \frac{R\_1B - S\_1B}{R\_1B}$$

Figure 18A:
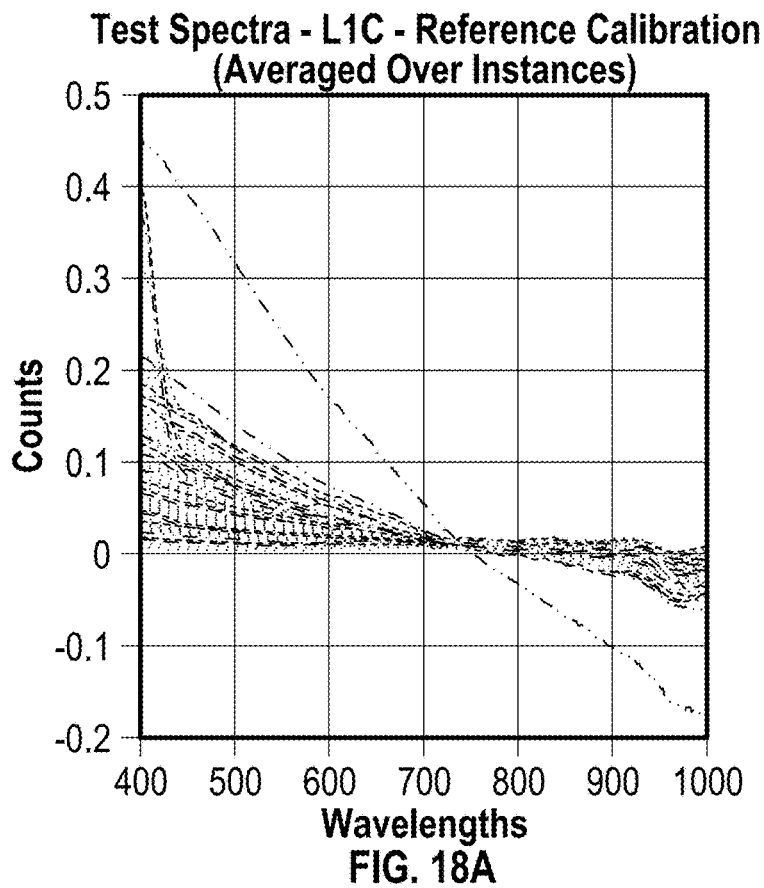
FIG. 18a depicts an example test spectra including spectra normalization averaged over instances.
Figure 18B:
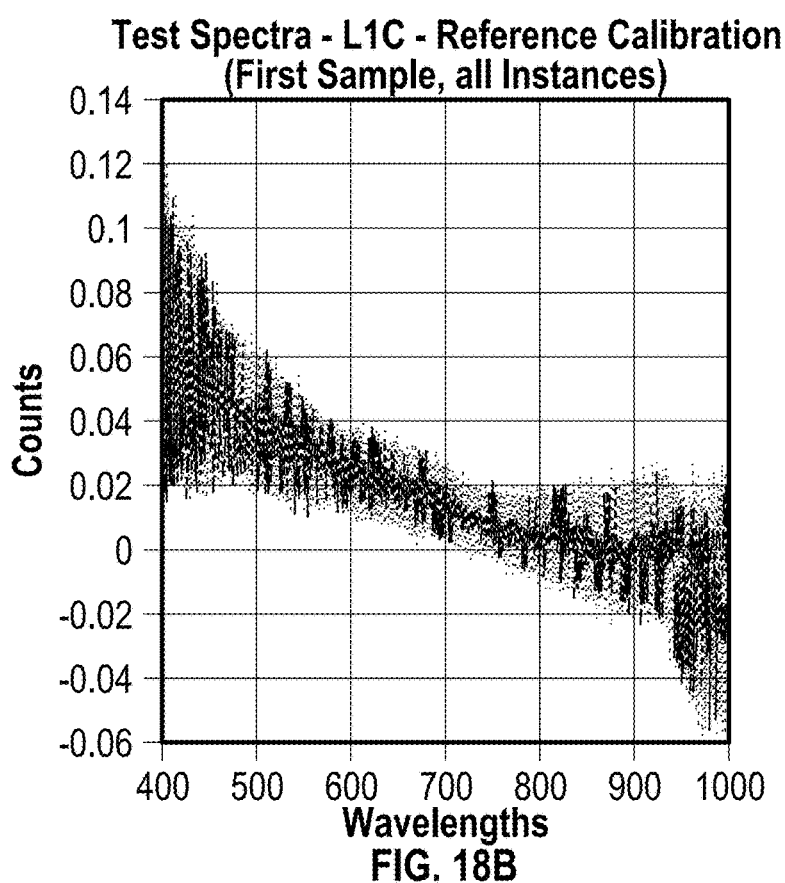
FIG. 18b depicts an example reference spectra including spectra normalization averaged over instances.

FIG. 18a depicts an example test spectra including spectra normalization averaged over instances. FIG. 18b depicts an example reference spectra including spectra normalization averaged over instances.

In step 1510, the digital device performs background removal and estimation. In one example, the digital device takes the ratio of the reference to the signal and then subtracts the reference.

It will be appreciated that samples are often more negative (uninfected) then positive. For example, the positive rate may be only 5% or less of all samples (e.g., 20 times more negatives than positives). In various embodiments, a background pool is created. Negative results may be clustered into families.

In various embodiments, the digital device groups results according to similarities. For example, the digital device may select two negative results and subtract them to get a minimum energy which may be used for a characteristic curve. In some embodiments, measurements of any number of samples may be divided into levels (e.g., based on similarities and/or measurements). There may be any number of levels. For example, similarities or measurements may be ordered or ranked based on intensity, energy, and/or wavelength. The ordered or ranked information may be divided into sets based on equal or unequal thresholds.

Each of the measurements or sets may be compared to each other and a minimum may be taken to get characteristics for each level. A pool of negatives (compare positive to negative) may be obtained. A pool of negatives refers to a collection of negative results (e.g., no infection indicated) as opposed to positive results (e.g., infection indicated).

The result may be assessed to determine the curve. A flat line, for example, may contain no information while a curve may indicate information related to virus infection. The digital device may remove the background from future signals/measurements to remove the background signature of saliva and VTM itself. The background pool of information may also be determined and minimized to find the minimum energy.

Figure 19A:
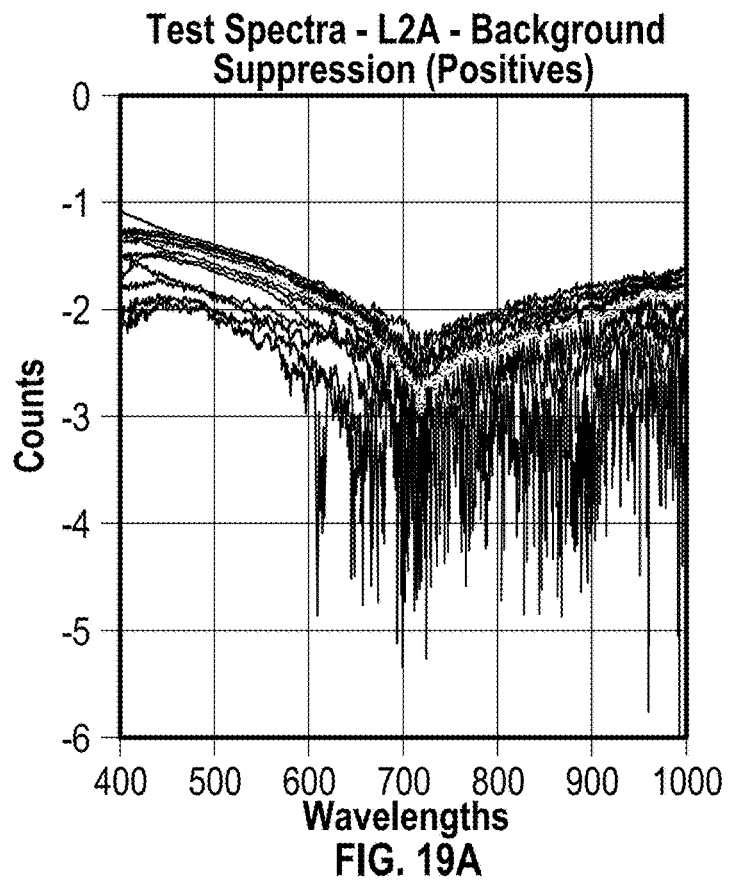
FIG. 19a depicts an example test spectra of positive (infection) results with background suppression.
Figure 19B:
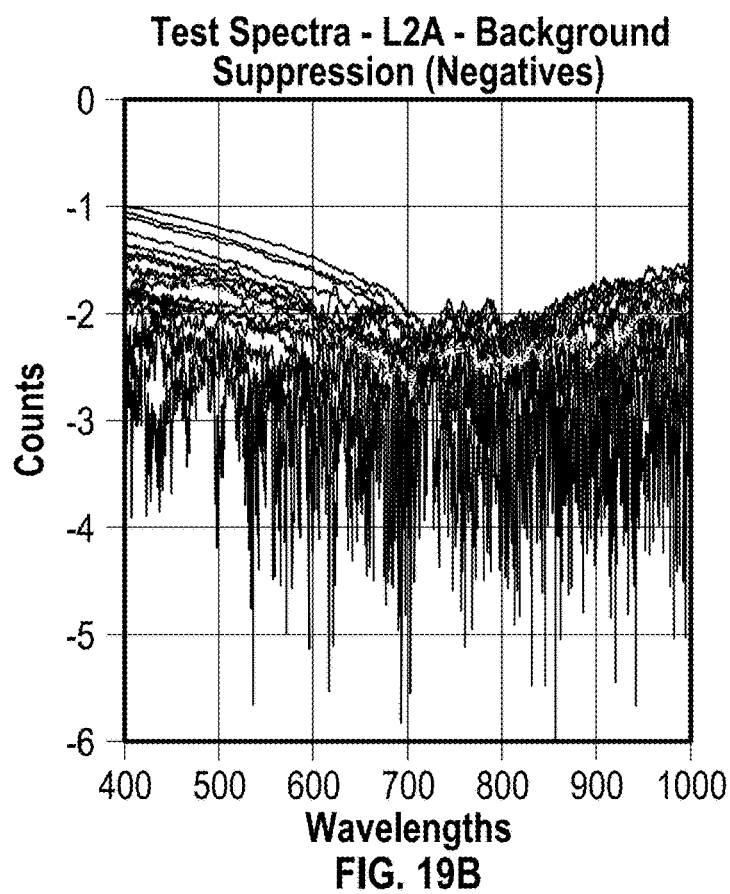
FIG. 19b depicts an example test spectra of negative (infection) results with background suppression.

FIG. 19a depicts an example test spectra of positive (infection) results with background suppression. FIG. 19b depicts an example test spectra of negative (infection) results with background suppression.

Figure 19C:
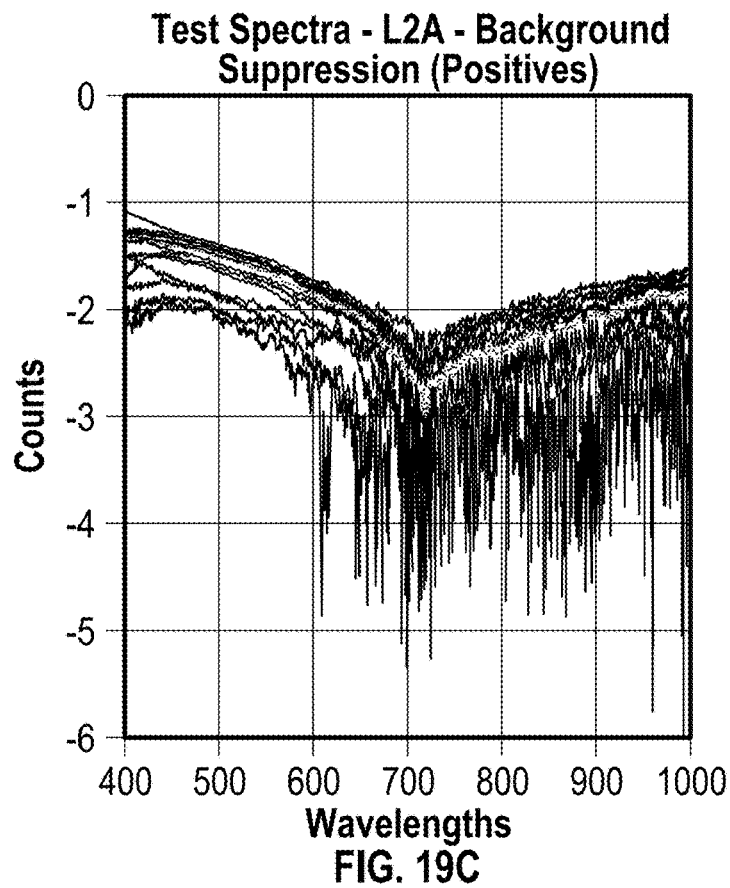
FIG. 19c depicts an example test spectra of positive (infection) results with background suppression.
Figure 19D:
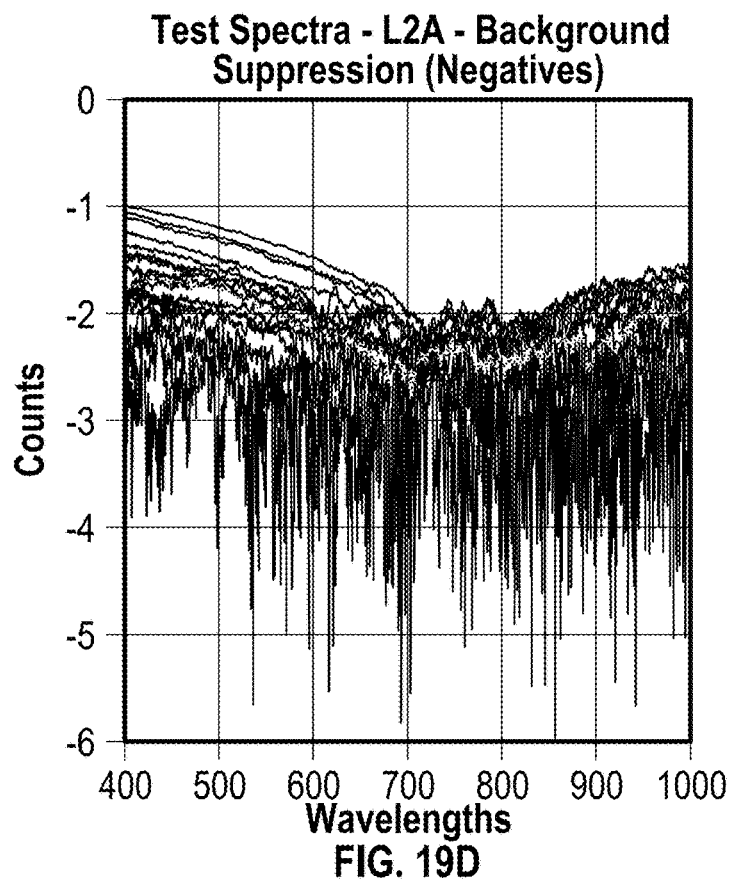
FIG. 19d depicts an example test spectra of negative (infection) results with background suppression.

FIG. 19c depicts an example test spectra of positive (infection) results with background suppression. FIG. 19d depicts an example test spectra of negative (infection) results with background suppression.

In step 1512, the digital device may perform lucky imaging background minimization. In various embodiments, the digital device and/or spectrometer may make many measurements of a sample. The digital device may assess the different samples to identify the sample that provides the most energy. For example, the digital device may perform background estimation and removal from any number of images (e.g., all or a subset) to identify the results that express the most information or an indication of a positive or negative result.

In step 1514, the digital device may perform wavelet scalogram conversion. In various embodiments, the digital device performs a wavelet decomposition. A wavelet may be selected and a cross correlation performed along the signal to measure intensities (e.g., weight on left of graph and wavelength along the X axis).

With background estimation, the difference between negatives and positives can be depicted. Intensity variations appear in high frequency wavelets which may indicate a spectral signature for infection (e.g., coronavirus).

Figure 20A:
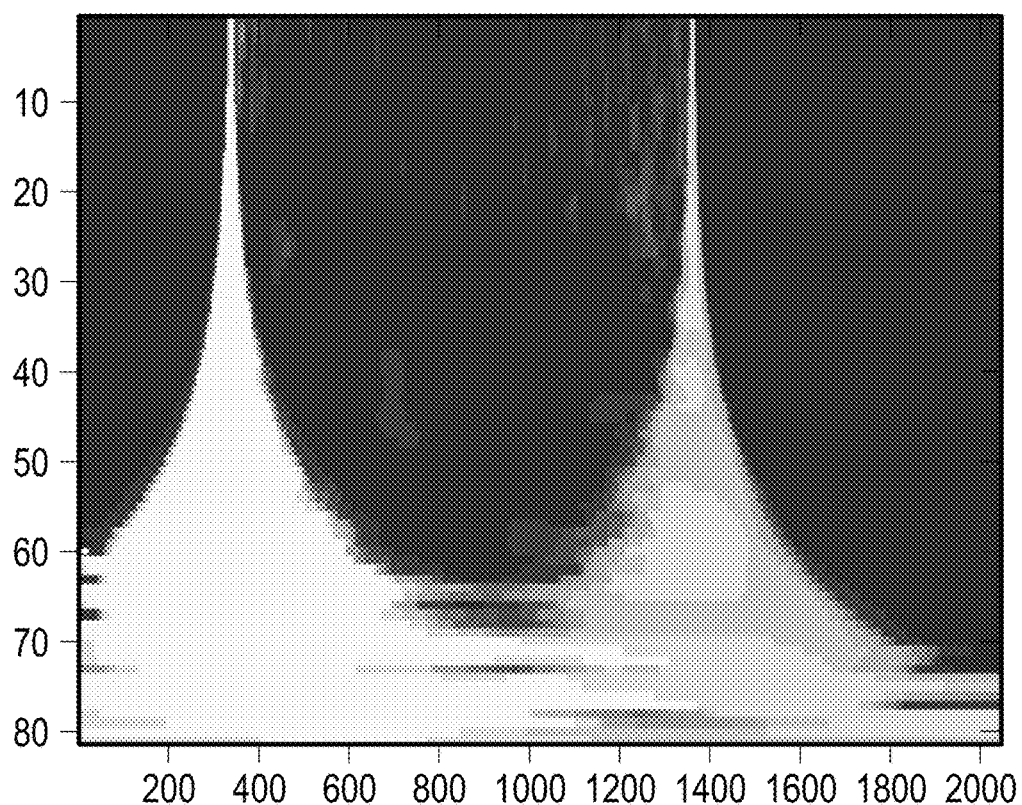
FIG. 20a depicts a negative result scalogram conversion after wavelet correlation.
Figure 20B:
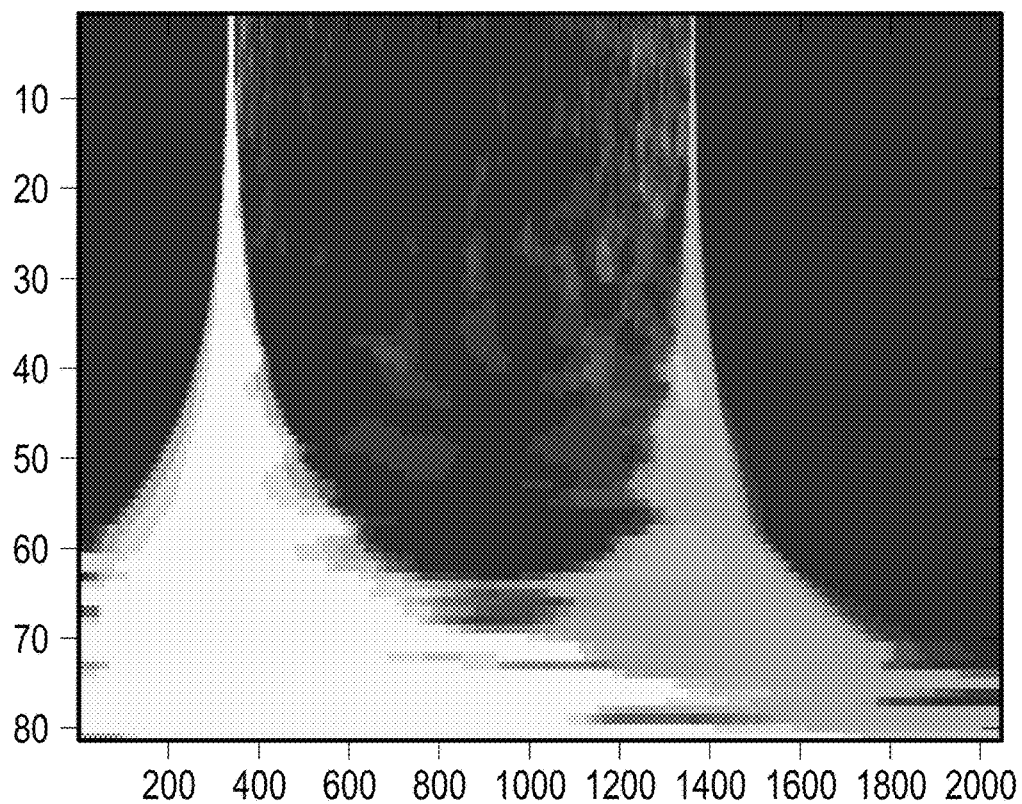
FIG. 20b depicts a positive result scalogram conversion after wavelet correlation.
Figure 20C:
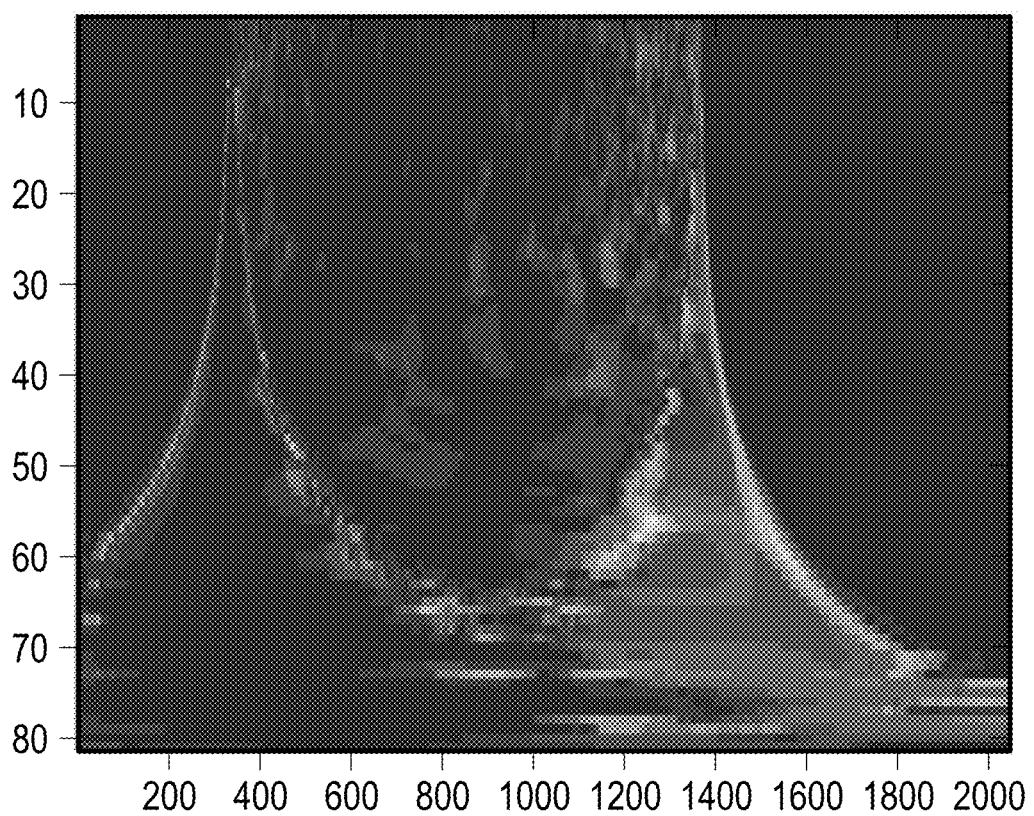
FIG. 20c depicts a difference between the positive and negative result scalogram conversion depicting the difference and indicating the signature of infection.

FIG. 20a depicts a negative result scalogram conversion after wavelet correlation. FIG. 20b depicts a positive result scalogram conversion after wavelet correlation. FIG. 20c depicts a difference between the positive and negative result scalogram conversion depicting the difference and indicating the signature of infection.

In various embodiments, the digital device may perform scalogram conversion after background removal to identify if the signature (e.g., intensities of absorption lines associated with a particular infection, virus-related protein, or virus) or pattern is present. In various embodiments, the digital device may perform the inverse wavelength transform.

Variations from sample to sample may create issues. In some embodiments, an autoexposure is used. For example, the digital device and/or the spectrometer may take an image of the spectral intensities and determine location in a fixed integration of time and determine the integration time to get to a desired measurement (e.g., 60,000 digital numbers).

Figure 21:
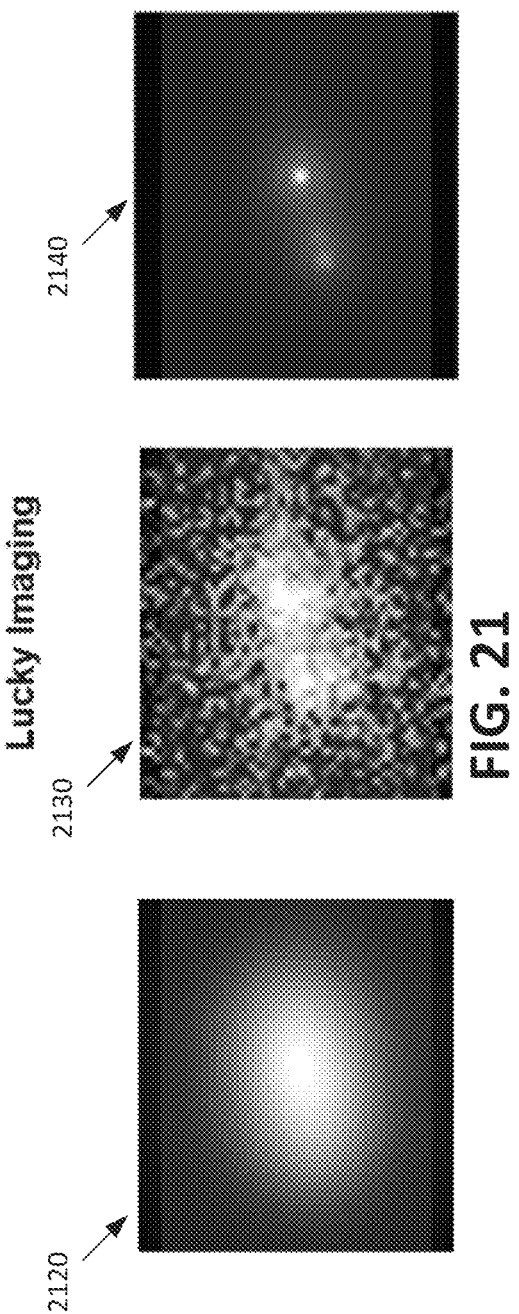
FIG. 21 depicts examples of lucky imaging in some embodiments.

FIG. 21 depicts examples of lucky imaging in some embodiments. In various embodiments, the spectrometer with a vortex mask and/or a Lyot stop may take multiple measurements of the same sample. The spectrometer or processor may select one or more images containing information most indicative of the presence of the virus (e.g., the spectral signature of the virus) or lack of presence of the virus. For example, luck imaging may utilize multiple measurements to select the image with the best relative clarity and accuracy (e.g., images that depict the energy for the wavelengths of interest associated with a virus). FIG. 21 depicts spectrometer output image 2120 which is improved using lucky imaging to rendered image 2130 which is further improved through lucky imaging to image 2140. There may be any number of measurements used for lucky imaging.

Combined with lucky imaging, a signal may be strengthened by processing many spectrogram snapshots together. In one example, multiple snapshots may be taken of the breath sample using a spectrometer with a vortex mask 840 as discussed herein. Lucky imaging enables using multiple measurements to improve clarity, reduce noise, and detect previously faded signals related to virus infection.

In various embodiments, the system described herein detects COVID-19 infections with a tested 87.5% accuracy. The detection and determination may take under 10 milliseconds.

A discriminator may also be used, in some embodiments. The discriminator may receive results from the spectrometer, assess the information, and provide an indication based on the results (e.g., classification of infection or not infected). In one example described herein, scalograms are collected and parts of the scalograms (e.g. the parts associated with the signature of the virus being tested for) may be compared against references or thresholds. Based on the comparison, the discriminator (e.g., classifier) may provide an indication of infection or not infected (or indeterminant).

In other embodiments, a convolutional neural network (CNN) may be used as a discriminator to identify measurements indicating infection and non-infection. In various embodiments, a neural network may be trained using measurements from the vortex spectrometer as discussed herein. The neural network may also be trained using laboratory test results to confirm those patrons that are infected and those that are not infected. The neural network may receive or generate a set of features base on the output (i.e., measurement results) of the vortex spectrometer. The neural network may then be tested to confirm predictions against known infection/noninfection results.

In one example, the neural network may identify wavelength intensities in the ranges of 735 nm, 780 nm, 810 nm, and 860 nm as being indicative of infection.

It will be appreciated that any discrimination may be utilized to identify infection and noninfected patrons and/or samples. For example, any statistical method, such as logistic regression analysis, may be utilized.

Figure 22:
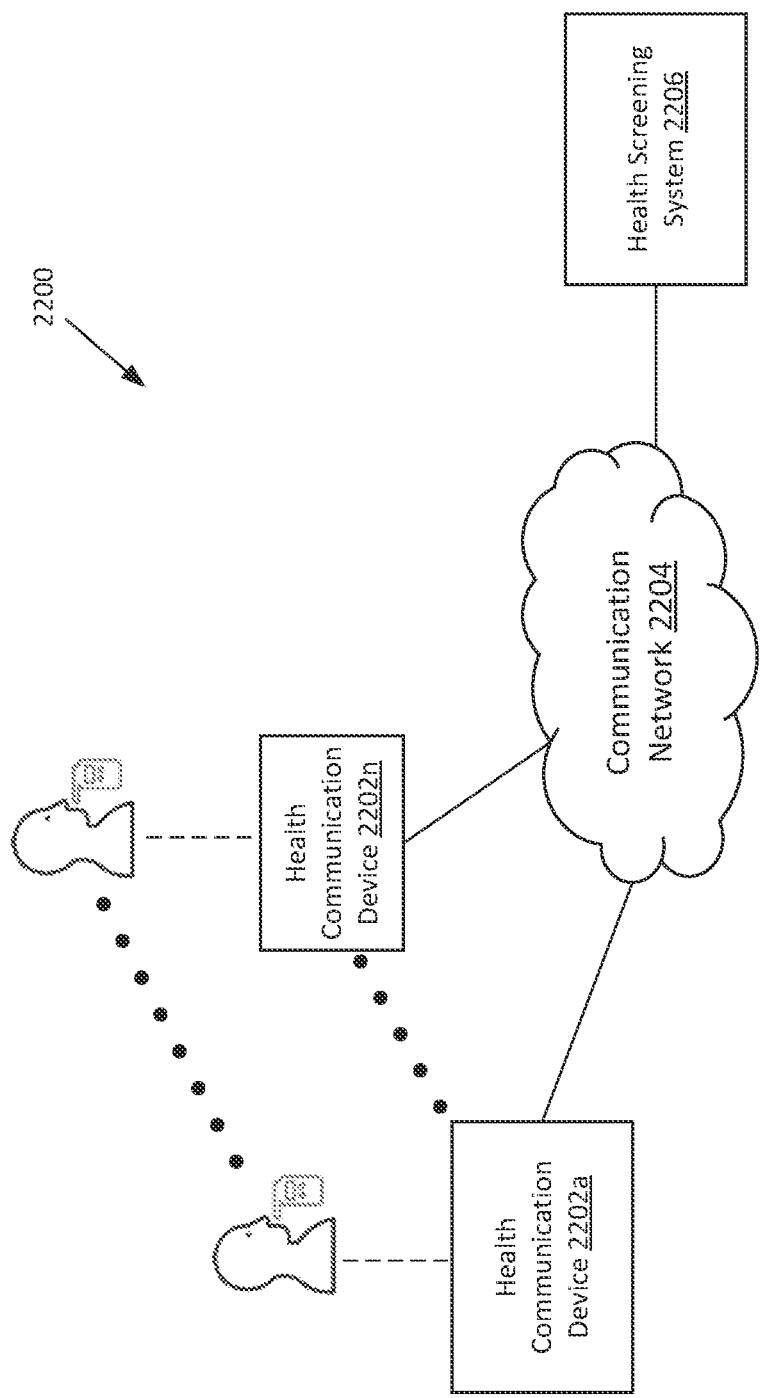
FIG. 22 depicts a health screening environment in some embodiments.

FIG. 22 depicts a health screening environment 2200 in some embodiments. The health screening environment 2200 includes health communication devices 2202a-2202n in communication with a health screening system 2206 over communication network 2204. The health communication devices 2202a-n are any type of digital device that may provide vortex spectrometer measurement results. A vortex spectrometer is any spectrometer with a vortex mask within the optical path.

The health communication devices 2202a-2202n may be, for example, any digital device. A digital device is any device with a processor and memory. In one example, health communication devices 2202a-2202n may include computers in communication with one or more vortex spectrometers. In another example, the health communication devices 2202a-2202n may each be a different vortex spectrometer capable of network communication.

In one example, patrons may each provide a sample. Samples may include exhalation into a breathalyzer, exhalation onto a fogging window, swabs, saliva swabs, or the like. Each of the samples may be placed within one or more vortex spectrometers for testing. The measurements results may be provided over the communication network 2204 to the health screening system 2206. Although the health screening system 2206 may be on a network (e.g., cloud-based), the health screening system 2206 may be on-premises (e.g., local to where the samples were taken or where the vortex spectrometer performed the test).

The health screening system 2206 may receive the measurement results and analyze the results. In various embodiments, the health screening system 2206 may receive many different measurement results from many different vortex spectrometers. The patrons and/or the vortex spectrometers may be geographically remote from each other. The health screening system 2206 may provide centralized testing and return health screening indications (e.g., categories) back to the health communication device that provided the measurement results.

By centralizing the health screening system 2206 on a network, the health screening system 2206 may take advantage of greater processing and memory resources, thereby enabling greater computational efficiency, speed, and scalability. Further, the health screening system 2206 may utilize the measurement results received from many different people and geographically diverse sources to assist with training statistical and/or AI models and curation.

Figure 23:
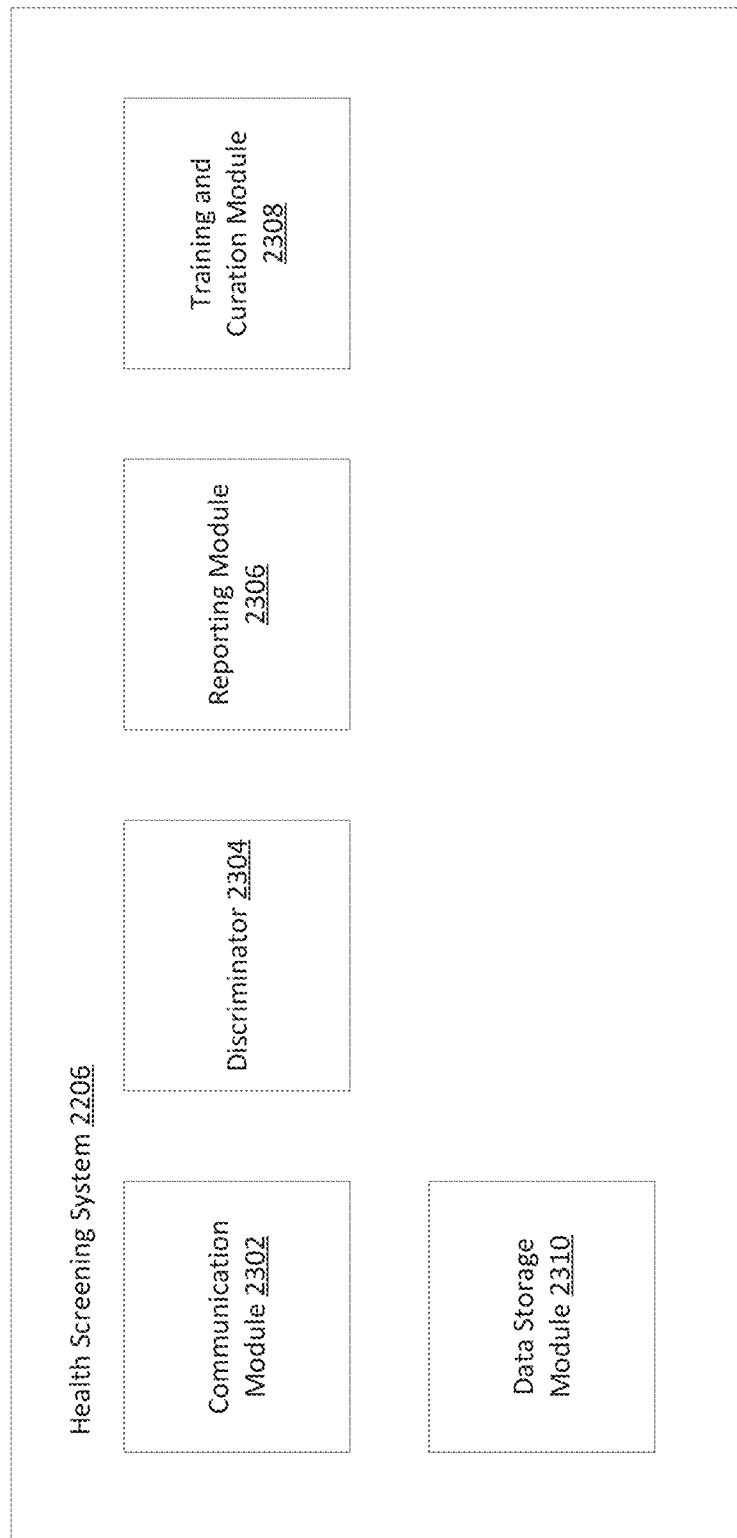
FIG. 23 depicts an example health screening system in some embodiments.

FIG. 23 depicts an example health screening system 2206 in some embodiments. The health screening system 2206 may include a communication module 2302, a discriminator 2304, a reporting module 2306, a training and curation module 2308, and a data storage module 2310.

The health screening system 2206 may be configured to aggregate information from across patients and test results to provide reporting. The reporting may be in real-time. In various embodiments, the health screening system 2206 may, at the simplest level, receive test results and/or vortex spectrometer measurements from any number of patients in any number of locations. The health screening system 2206 may provide indications of infection (e.g., infected, not infected, likely infected, unlikely infected, or unknown) back to the device that provided the measurement results. In some embodiments, the health screening system 2206 may aggregate the information and provide reporting indicating that the number of virus infections detections and the number of tests performed.

The communication module 2302 may receive spectrometer measurements of samples provided by patrons. In one example the communication module 2302 may receive a variety of different spectrometer measurements from any number of spectrometers regarding any number of patron samples. The patron sample may be sample of the patron's breath, saliva, or swab sample, or the like. The communication module 2302 may receive spectrometer measurements from any number of health communication devices 2202a-n.

The discriminator 2304 may receive and analyze the spectrometer measurements to categorize the results. Categories may include, for example, infected, not infected, likely infected, likely not infected, unknown, or any other labels. The discriminator 2304 may utilize statistical approaches, such as logistic regression, and/or AI modeling techniques such as convolutional neural networks.

In the example discussed herein, the discriminator 2304 may utilize scalograms of those known to be infected to identify areas of the graph associated with infection (e.g., by comparing scalograms of those known to not be infected). Infection or lack of infection, for example, may be confirmed by reagent test or other testing. The indication of infection based on a part of the scalogram(s) may be used as a reference. New test results may be used to generate information associated with all or part of the reference to indicate infection.

It will be appreciated that scalograms may not need to be generated to indicate infection. Rather, the discriminator 2304 may identify wavelength intensities from results of a vortex spectrometer associated with infection (e.g., as learned from the previous testing with known infections) and categorize those who are infected and not infected.

The degree to which new test results from new patients match the reference information (e.g., degree of confidence or fit) may be compared to a threshold to determine infection (e.g., above a particular degree of confidence or fit) or lack of infection (e.g., below a particular degree of confidence or fit).

Once the discriminator 2304 analyzes and categorizes the spectrometer results, infection indications such as health screening indications (e.g., "infected" or 'not-infected") may be returned to the health communication device that provided the original spectrometer measurements.

The discriminator 2304 may also store these spectrometer measurements and/or results of the categorization analysis in the data storage module 2310.

In various embodiments, the discriminator 2304 may apply a logistic fit (e.g., a probability curve). Alternately, the discriminator 2434 may perform as a match filter.

In one example, the discriminator 2304 assesses a negative case (e.g., non-infected case) using large ensemble sampling. Similarly, the discriminator 2304 may assess a positive case. The discriminator 2304 may create a spectral curve of a negative case (of non-infection) and spectral curve of a positive case (of infection). The discriminator 2304 may create a characteristic curve for negative using a mean estimation over a sample size (e.g., 75,000 instances) after normalization. The negative characteristic curve is then used as a reference. The discriminator 2304 may take the (reference sample—the positive sample) divided by the reference sample to create a characteristic curve for infection. The discriminator 2304 may compare new spectral measurements and curves to the characteristic curve to determine likelihood of infection or categories of infection (e.g., based on the degree of fit to the characteristic curve for infection). A threshold may be set based on how known data fits the curve (e.g., based on known infection information and known uninfected information).

In some embodiments, the discriminator 2304 may utilize a bandpass of wavelengths using the characteristic curve for infection to create a window (e.g., a bandpass of wavelengths), assess mean value and standard deviation of the value, roll the window through the spectrum and iterate. The discriminator 2304 may plot the standard deviation vs. the mean for positive and negatives to identify wavelength bands that separate. This may be used as a method for separating information—for certain wavelengths, there may be significant separation and thereby enabling easy identification of infection vs. noninfection.

The reporting module 2306 may assess and aggregate the information including spectrometer measurements from any location, any spectrometer, any patrons, or the like as well as the categorized labels. As a result, the reporting module 2306 may be able to provide reports regarding infection rates in geographic areas, types of patrons, success of vaccinations, and/or the like.

The training and curation module 2308 may training and/or curate the statistical approaches and/or AI modeling techniques based on the received spectrometer measurements and the results from the discriminator 2304. It will be appreciated that the training and curation module 2308 will enable improvements is statistical analysis and AI modeling because of the variety and amount of data received from numerous geographically remote and diverse sources. As a result, the training and curation module 2308 may improve accuracy, speed of analysis, and scalability of future testing.

The data storage module 2310 may store spectrometer measurements and/or output from the discriminator 2304. In some embodiments, data stored in the data storage module 2310 may be stripped of personally identifying information. Since the stored data may be used for aggregate reporting, training, and/or curation, personally identifying information may not be necessary to store.

The data storage module 2310 may be encrypted. Further, communication between the health communication devices 2202a-n and the communication module 2302 may be encrypted (e.g., via VPN) and/or authenticated (e.g., through the use of encryption keys and/or digital certificates).

A module may be hardware, software, or a combination of both hardware and software. A hardware module may be a chip (e.g., ASIC) or the like. Software may be executed by a processor. Although a limited number of modules are depicted in the figure, there may be any number of modules. Further, individual modules may perform any number of functions, including functions of multiple modules as shown herein.

Figure 24:
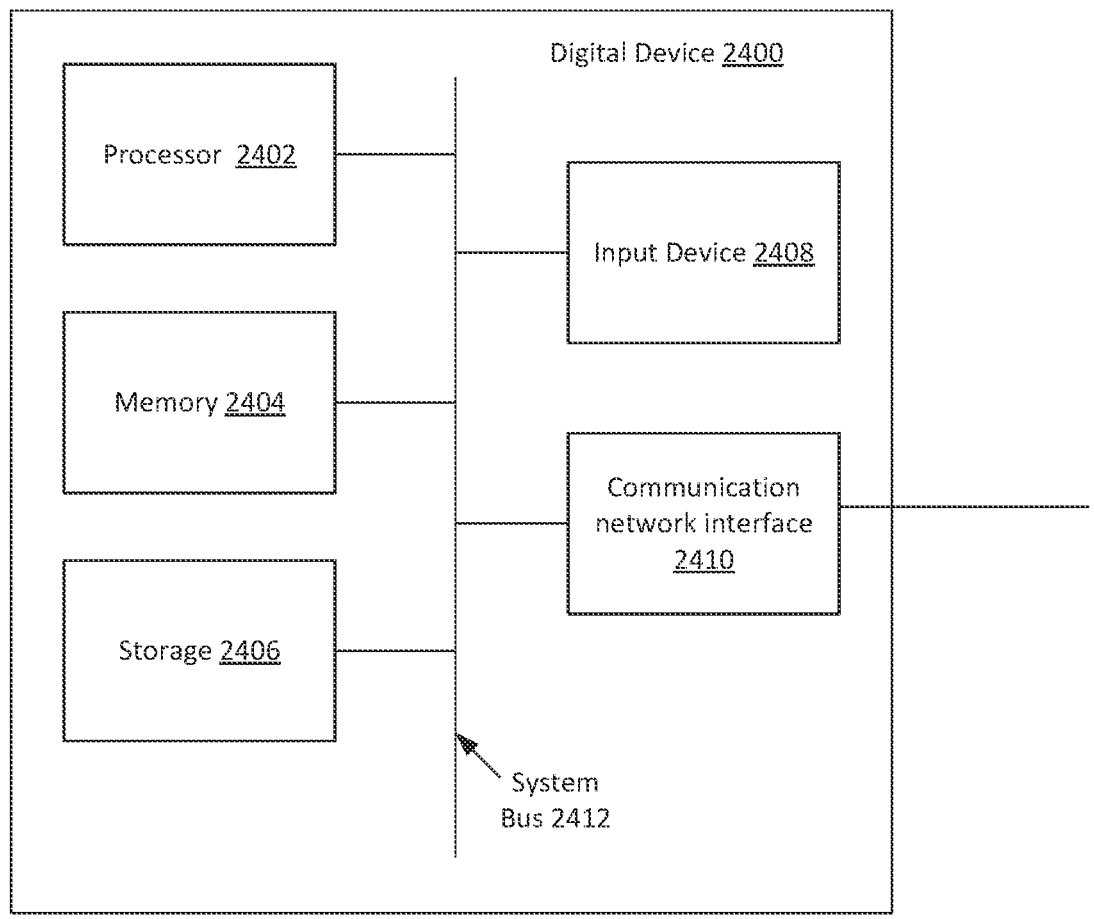
FIG. 24 depicts a block diagram of an example digital device according to some embodiments.

FIG. 24 depicts a block diagram of an example digital device 2400 according to some embodiments. Digital device 2400 is shown in the form of a general-purpose computing device. Digital device 2400 includes processor 2402, RAM 2404, storage 2406, input/output device 2408, communication interface 2410, and a system bus 2412 that couples various system components including storage 2406 to processor 2402.

System bus 2412 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Digital device 2400 typically includes a variety of computer system readable media. Such media may be any available media that is accessible by the digital device 2400 and it includes both volatile and nonvolatile media, removable and non-removable media.

In some embodiments, processor 2402 is configured to execute executable instructions (e.g., programs). In some embodiments, the processor 2402 comprises circuitry or any processor capable of processing the executable instructions.

In some embodiments, RAM 2404 stores data. In various embodiments, working data is stored within RAM 2404. The data within RAM 2404 may be cleared or ultimately transferred to storage 2406.

In some embodiments, digital device 2400 is coupled to a network via communication interface 2410. Such communication can occur via Input/Output (I/O) device 2408. Still yet, the digital device 2400 may communicate with one or more networks such as a local area network (LAN), a general wide area network (WAN), and/or a public network (e.g., the Internet).

In some embodiments, input/output device 2408 is any device that inputs data (e.g., mouse, keyboard, stylus) or outputs data (e.g., speaker, display, virtual reality headset).

In some embodiments, storage 2406 can include computer system readable media in the form of volatile memory, such as read-only memory (ROM) and/or cache memory. Storage 2406 may further include other removable/non-removable, volatile/non-volatile computer system storage media. By way of example only, storage 2406 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CDROM, DVD-ROM or other optical media can be provided. In such instances, each can be connected to system bus 2412 by one or more data media interfaces. As will be further depicted and described below, storage 2406 may include at least one program product having a set (e.g., at least one) of program modules that are configured to carry out the functions of embodiments. In some embodiments, RAM 2404 is found within storage 2406.

Program/utility, having a set (at least one) of program modules may be stored in storage 2406 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments as described herein. A module may be hardware (e.g., ASIC, circuitry, and/or the like), software, or a combination of both.

It should be understood that although not shown, other hardware and/or software components could be used in conjunction with the digital device 2400. Examples include, but are not limited to: microcode, device drivers, redundant processing units, external disk drive arrays, RAID systems, tape drives, and data archival storage systems, etc.

Exemplary embodiments are described herein in detail with reference to the accompanying drawings. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

As will be appreciated by one skilled in the art, aspects of one or more embodiments may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program, for use by, or in connection with, an instruction execution system, apparatus, or device.

A computer readable signal medium may include a propagated data signal with computer readable program code embodied therein, for example, in baseband/or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program, for use by, or in connection with, an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects discussed herein may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider)1

Aspects of some of the embodiments are described herein with reference to flowchart illustrations and/or block diagrams of methods, apparatus (systems) and computer program products according to embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a nontransitory computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

It may be apparent to those skilled in the art that various modifications may be made and other embodiments may be used without departing from the broader scope of the discussion herein. Therefore, these and other variations upon the example embodiments are intended to be covered by the disclosure herein.

The invention claimed is:

1. A system comprising:
   at least one light source configured to generate a light of at least one wavelength and project the light over an optical path;
   a sample device, the device containing a sample obtained from exhalation of a person, the sample device being transparent and being at least partially within the optical path;
   a vortex mask being within the optical path and configured to receive the light after the light passes through at least a portion of the sample device, the vortex mask including a series of concentric circles etched in a substrate, the vortex mask configured to provide destructive interference of coherent light received from the at least one light source;
   a detector configured to detect and measure wavelength intensities from the light in the optical path, the wavelength intensities being impacted by the light passing through the sample, the detector receiving the light that remained after passing through the vortex mask; and
   a processor configured to provide measurement results based on the wavelength intensities.

2. The system of claim 1, further comprising a discriminator configured to analyze the measurement results and identify a category associated with the measurement results.

3. The system of claim 2, wherein the discriminator utilizes logistic regression to categorize the measurement results.

4. The system of claim 1, wherein the sample is obtained from a breathalyzer provided to a person.

5. The system of claim 4, wherein the breathalyzer cools a cuvette which condenses the sample of an exhalation of the person within the sample device, the sample device being removable from the breathalyzer.

6. The system of claim 1, further comprising a lyot mask positioned in the optical path and configured to receive light from the vortex mask and provide the light towards the detector, the lyot mask configured to relocate residual light away from a region of an image plane, thereby reducing light noise from the at least one light sources and improving sensitivity to off-axis scattered light.

7. The system of claim 6, wherein the lyot mask is a lyot-plane phase mask.

8. The system of claim 1, wherein the vortex mask is an optical vortex coronagraph that uses a phase-mask in which a phase-shift varies azimuthally around a center to mask light along a center axis of the optical path but allows light from off-axis.

9. The system of claim 1, wherein the at least one light source configured to generate the light of at least one wavelength comprises two light sources, each configured to provide a different wavelength.

10. The system of claim 1, wherein the at least one light source configured to generate the light of at least one wavelength comprises a single light source that generates several wavelengths, the system further comprising a diffraction grating to separate out different wavelengths for propagating down the optical path.

11. The system of claim 1, wherein the at least one light source configured to generate the light of at least one wavelength comprises generating wavelengths at 735 nm, 780 nm, 810 nm, and 860 nm.

12. The system of claim 1, wherein the sample may indicate infection by COVID-19.

13. A method comprising:
   generating, by at least one light source, a light of at least one wavelength and project the light over an optical path;
   receiving, by a sample device, the light from the at least one optical source, the device containing a sample obtained from exhalation of a person, the sample device being transparent and being at least partially within the optical path;
   providing destructive interference of coherent light passed through the sample device using a vortex mask, the vortex mask including a series of concentric circles etched in a substrate;
   measuring, by a detector, wavelength intensities of the light after having passed through the vortex mask; and
   providing measurement results based on wavelength intensities.

14. The method of claim 13, further comprising analyzing the measurement results and categorizing the measurement results with a discriminator.

15. The method of claim 14, wherein analyzing the measurement results and categorizing the measurement results comprises performing logistic regression to categorize the measurement results.

16. The method of claim 13, wherein the sample is obtained from a breathalyzer provided to a person.

17. The method of claim 16, wherein the breathalyzer cools a cuvette which condenses the sample of an exhalation of the person within the sample device, the sample device being removable from the breathalyzer.

18. The method of claim 13, further comprising relocating residual light received form the vortex mask away from a region of an image plane, thereby reducing light noise from the at least one light source and improving sensitivity to off-axis scattered light.

19. The method of claim 18, wherein relocating residual light away from a region of the image plane is performed with a lyot-plane phase mask.

20. The method of claim 13, wherein the vortex mask is an optical vortex coronagraph that uses a phase-mask in which a phase-shift varies azimuthally around a center to mask light along a center axis of the optical path but allows light from off-axis.

21. The method of claim 13, wherein generating, by at least one light source, a light of at least one wavelength and project the light over an optical path comprises generating two wavelengths from two different light sources.

22. The method of claim 13, wherein generating, by at least one light source, a light of at least one wavelength and project the light over an optical path comprises generating several wavelengths from a single light source and separating desired wavelengths to propagate along the optical path.

23. The method of claim 13, wherein generating, by at least one light source, a light of at least one wavelength and project the light over an optical path comprises generating wavelengths at 735 nm, 780 nm, 810 nm, and 860 nm.

24. The method of claim 13, wherein the sample may indicate infection by COVID-19.

* * * * *